United States Patent [19]
Nuri et al.

[11] Patent Number: 6,143,571
[45] Date of Patent: Nov. 7, 2000

[54] METHOD FOR ANALYTICALLY DETERMINING OXYGEN FOR EACH FORM OF OXIDE

[75] Inventors: Yoshio Nuri; Tomoko Ise; Yoshiyuki Kato, all of Himeji, Japan

[73] Assignee: Sanyo Special Steel Co., Ltd., Himeji, Japan

[21] Appl. No.: 09/113,192

[22] Filed: Jul. 10, 1998

[30] Foreign Application Priority Data

| Jul. 11, 1997 | [JP] | Japan | 9-186273 |
| Aug. 20, 1997 | [JP] | Japan | 9-223984 |
| Sep. 8, 1997 | [JP] | Japan | 9-243039 |
| Jan. 19, 1998 | [JP] | Japan | 10-007785 |

[51] Int. Cl.[7] .................................................. G01N 33/20
[52] U.S. Cl. .......................... 436/75; 73/19.07; 436/127; 436/157; 436/164; 436/181
[58] Field of Search .............. 436/75, 157, 127, 436/164, 181; 73/19.07

[56] References Cited

U.S. PATENT DOCUMENTS 4,229,412  10/1980  Orths et al. ................................ 422/80

FOREIGN PATENT DOCUMENTS

| 6-148167 | 5/1994 | Japan . |
| 6-148170 | 5/1994 | Japan . |

OTHER PUBLICATIONS

Prumbaum et al., Giessereforschung, vol. 31 (2–3), pp. 71–82, 1979.

*Primary Examiner*—Jan Ludlow
*Attorney, Agent, or Firm*—Armstrong, Westerman, Hattori, McLeland & Naughton

[57] ABSTRACT

The method for analyzing a metal for oxygen, using inert gas carrying fusion/infrared absorption analysis, having the steps of: placing a metal analyte in a graphite crucible; heat-melting the metal analyte; extracting a gas from the melt bath; and analyzing the gas to determine the total oxygen content of the metal in the form of a plurality of separated waves, wherein the metal analyte is heated at a temperature rise rate of not more than 20° C./sec in a period from a starting point A of a first wave to a peak point B of the first wave, held at a constant temperature in a period from the peak point B of the first wave to an end point C of the first wave, and, after the completion of the appearance of the first wave, is heated to melt the metal analyte for further analysis.

3 Claims, 7 Drawing Sheets

METHOD FOR ANALYTICALLY DETERMINING OXYGEN FOR EACH FORM OF OXIDE

BACKGROUND OF THE INVENTION

1. Technical Field of the Invention

The present invention relates to analysis of analytes, such as metals, refractories, and slag, for the content of oxygen or oxide. More particularly, the present invention relates to a method and apparatus for analyzing an analyte for the content of oxygen or oxide for each oxide, wherein oxygen contained in an analyte is extracted as CO gas which is then measured by inert gas carrying/infrared absorption analysis.

2. Description of the Prior Art

In recent years, an analytical technique for accurately and rapidly analyzing an analyte for the content of oxygen or oxide has been desired in the art.

For example, in the field of steelmaking, the development of ultra low oxygen steel or high purity iron with the form of oxides being controlled has been progressed, and quantitatively determining the oxygen concentration on a very low level of ppm (parts per million) with high accuracy has been required. To this end, at the time of analyzing an analyte for a very small amount of oxygen, a contaminant, such as an oxide film, formed on the surface of the analyte should be removed. Electrolytic polishing or chemical polishing has been used for pretreatment at the time of analysis for oxygen wherein contaminants, such as an oxide film, are removed.

The electrolytic polishing is a method wherein contaminants, such as an oxide film, formed on the surface of an analyte is removed with a nonaqueous solvent electrolyte, such as a 10% acetylsalicyclic acid/1% tetramethylammonium chloride/methyl alcohol solution or a 4% sulfosalicyclic acid/1% lithium chloride/methyl alcohol solution. On the other hand, the chemical polishing is a method wherein an iron and steel analyte is immersed in a solution, such as hydrogen fluoride/hydrogen peroxide (HF-$H_2O_2$), to remove a contaminant, such as an oxide film, formed on the surface of the analyte (for example, Hisao Yasuhara et al.: CAMP-ISIJ, 10(1997), p. 709).

However, the amount of oxygen present as an oxide on the surface of the analyte is not constant. For example, the amount of the surface oxide removed varies depending upon a polishing solution, a polishing time or the like, leading to a large variation in analytical value. Further, electrolytic polishing or chemical polishing of the surface of the analyte is disadvantageous in that the pretreatment of the analyte is troublesome and requires a lot of time.

In order to solve the above problem, a method for analyzing an iron and steel for a very small amount of oxygen has been proposed (Japanese Patent Laid-Open No. 148170/1994). This method comprises the steps of: grinding the surface of an iron and steel analyte by means of a grinder, a file or the like; heat-extracting a very small amount of oxygen contained in the analyte; and determining the extracted oxygen, wherein the analyte after the grinding is placed in a carbon crucible and preheated at a temperature of 900 to 1400° C. to separate and determine oxygen derived from contaminants, such as deposited oxygen and an oxide film, on the surface of the analyte and oxygen in the iron and steel in the form of an oxide inclusion.

The analysis of an analyte for the content of oxygen by the above proposed method, however, has a problem that a point, where oxygen is evolved from an oxide inclusion (point D shown in FIG. 1), overlaps with the first wave, although the degree of overlapping varies depending upon the type, amount, and particle diameter distribution of oxide inclusions. This causes a part of the oxygen evolved from the oxide inclusion to be embraced in the amount of oxygen evolved from the surface deposited oxygen and iron oxide, making it impossible to accurately determine only the amount of oxygen evolved from the oxide inclusion.

On the other hand, in a bearing steel used under severe conditions, particularly $Al_2O_3$, $MgO \cdot Al_2O_3$, and $(Ca, Mg)O \cdot Al_2O_3$ inclusions, among inclusions present in a very small amount, are likely to form large grains causative of fatigue failure. For this reason, a reduction in amount of inclusions in the product and the control of the form of inclusions are important, and a technique, which can accurately and rapidly analyze a low oxygen steel for each inclusion, has been desired in the art.

Conventional methods for analyzing a steel for inclusions include: a method which comprises extracting a specimen from an analyte, observing a test surface under a microscope, and classifying inclusions into A to C series (JIS G 0555); and a method wherein the surface of an analyte is subjected to mirror polishing and then instrumentally analyzed by electron beam microanalysis or the like.

In these methods, however, only a certain cross section of the analyte is analyzed. This poses problems including that true inclusions causative of material failure cannot be detected, the measuring time taken is very long, and pretreatment of the analyte, such as polishing, is troublesome.

An analytical method using an oxygen analyzer has recently been proposed as means for solving these problems (Japanese Patent Laid-Open No. 148167/1994). In this method, an analyte is placed in a graphite crucible and continuously heated at a constant temperature rise rate to separate oxygen derived from easily reducible oxides (such as FeO and MnO), which are decomposed on a relatively low temperature side, and oxygen derived from sparingly reducible oxides (such as CaO and $Al_2O_3$), which are decomposed on a relatively high temperature side, from each other utilizing a CO gas extraction curve at the time of analysis.

The method described in Japanese Patent Laid-Open No. 148167/1994 is intended for a high content of oxygen of not less than 10% in steelmaking slag, and application of this method to a metal analyte containing oxygen in a very small amount on the order of several ppm has revealed that peaks in CO gas extraction curves are small and waves in respective CO gas extraction curves overlap with each other or one another, making it difficult to separate waves from each other or one another, that is, making it difficult to apply the above method to a metal analyte containing oxygen in a very small amount on the order of several ppm. Further, the above method is intended for separation of oxygen derived from easily reducible oxides and oxygen derived from sparingly reducible oxides and cannot be applied to analysis for oxygen in each oxide inclusion present in a very small amount.

SUMMARY OF THE INVENTION

An object of the present invention is to provide a method for analyzing an iron and steel for the content of oxygen that, without pretreatment of the iron and steel to remove an oxide film as a contaminant formed on the surface of the iron and steel, can accurately separate and determine oxygen derived from the oxide film as the contaminant and oxygen contained in the iron and steel in the form of oxide inclusions.

Another object of the present invention is to provide a method and apparatus for analyzing an analyte for the content of oxygen or oxide in each oxide, especially a method and apparatus that can accurately and rapidly analyze the analyte even when the oxygen content or oxide content is very low.

Characteristic features of the present invention are as follows.

(1) A method for analyzing a metal for oxygen, using inert gas carrying fusion infrared absorption analysis, comprising the steps of: placing a metal analyte in a graphite crucible; heat-melting the metal analyte; extracting a gas from the melt bath; and analyzing the gas to determine the total oxygen content of the metal in the form of a plurality of separated waves, wherein the metal analyte is heated at a temperature rise rate of not more than 20° C./sec in a period from a starting point A of a first wave to a peak point B of the first wave, held at a constant temperature in a period from the peak point B of the first wave to an end point C of the first wave, and, after the completion of the appearance of the first wave, is further heated to melt the metal analyte for further analysis.

(2) A method for analyzing an iron and steel for oxygen present in a very small amount, comprising the steps of: placing an iron and steel analyte in a graphite crucible in an inert gas atmosphere; heat-melting the analyte; extracting a CO gas from the melt bath; and analyzing the gas to determine the oxygen content of the iron and steel in the form of a plurality of separated waves, wherein the iron and steel analyte is heated so as not to exceed 900° C. in a period from the initiation of heating of the iron and steel analyte to the end point of a wave, which has appeared at a temperature below 900° C. and closest to 900° C., and subsequently further heated for analysis.

(3) A method for analyzing a metal for oxygen for each oxide inclusion, comprising the steps of: placing a metal analyte i a graphite crucible in an inert gas atmosphere; heat-melting the metal analyte; extracting a CO gas from the melt bath; and analyzing the gas to determine the oxygen content of the metal in the form of a plurality of separated waves, wherein, for each wave which appears at a temperature of 900° C. or above, the following temperature control pattern of ①, ②, and ③ is repeated:

① the analyte is heated at a temperature rise rate of not more than 2° C./sec in a period from a starting point $A_n$ of each wave to a peak point $B_n$ of each wave;

② the analyte is held at a constant temperature in a period from the peak point $B_n$ of each wave to an end point $C_n$ of each wave; and ③ the analyte is heated at a temperature rise rate of not more than 2° C./sec in a period from the end point $C_n$ of each wave to a starting point $A_{n+1}$ of the next wave.

(4) A method for analyzing an analyte for oxygen for each oxide, comprising the steps of: heating an analyte in an inert atmosphere; reacting the analyte with a carbon source while regulating the temperature rise rate; extracting a CO gas successively generated as a result of a reaction of oxygen in the analyte with the carbon source into an inert gas stream; successively analyzing the extracted CO gas by infrared absorption to determine the amount of reacted oxygen; detecting a peak of the amount of reacted oxygen from successively obtained data on the amount of reacted oxygen; carrying out the analysis while reducing the flow rate of the inert gas stream for each appearance of the detected peak corresponding to the amount of reacted oxygen to accumulate the data on the amount of reacted oxygen in time sequence; and determining the content of oxygen for each oxide in the analyte from the accumulated data on the amount of reacted oxygen.

(5) A method for analyzing an analyte for oxygen for each oxide, comprising the steps of: heating an analyte in an inert atmosphere; reacting the analyte with a carbon source while regulating the temperature rise rate; extracting a CO gas successively generated as a result of a reaction of oxygen in the analyte with the carbon source into an inert gas stream; successively measuring the amount of extracted CO gas by infrared absorption; detecting a peak of the amount of evolved CO from successively obtained data on the amount of evolved CO; carrying out the analysis while reducing the flow rate of the inert gas stream for each appearance of the detected peak corresponding to the amount of evolved CO to accumulate the data on the amount of evolved CO in time sequence; and determining the content of oxygen for each oxide in the analyte from the accumulated data on the amount of evolved CO.

(6) A method for analyzing an analyte for an oxide, comprising the steps of: heating an analyte in an inert atmosphere; reacting the analyte with a carbon source while regulating the temperature rise rate; extracting a CO as successively generated as a result of a reaction of oxygen in the analyte with the carbon source into an inert gas stream; successively analyzing the extracted CO gas by infrared absorption to determine the amount of reacted oxygen; detecting a peak corresponding to the amount of reacted oxygen from successively obtained data on the amount of reacted oxygen; carrying out the analysis while reducing the flow rate of inert gas stream for each appearance of the detected peak of the amount of reacted oxygen to accumulate the data on the amount of reacted oxygen in time sequence; determining the content of oxygen for each oxide in the analyte from the accumulated data on the amount of reacted oxygen; and determining the content of oxide from the content of oxygen for each oxide.

(7) A method for analyzing an analyte for an oxide, comprising the steps of: heating an analyte in an inert atmosphere; reacting the analyte with a carbon source while regulating the temperature rise rate; extracting a CO gas successively generated as a result of a reaction of oxygen in the analyte with the carbon source into an inert gas stream; successively measuring the amount of extracted CO gas by infrared absorption; detecting a peak corresponding to the amount of evolved CO from successively obtained data on the amount of evolved CO; carrying out the analysis while reducing the flow rate of the inert gas stream for each appearance of the detected peak of the amount of evolved CO to accumulate the data on the amount of evolved CO in time sequence; determining the content of oxygen for each oxide in the analyte from the accumulated data on the amount of evolved CO; and determining the content of each oxide from the content of oxygen for each oxide.

(8) An oxygen analyzer for each oxide in an analyte, comprising: analyte heating means for heating an analyte in an inert atmosphere while regulating the temperature rise rate; carbon source feeding means for feeding a carbon source for a reaction with oxygen in the analyte; inert gas stream generating means for generating an inert gas stream for extracting and carrying a CO gas generated as a result of a reaction of oxygen in the analyte with the carbon source; means for measuring the amount of reacted oxygen which analyzes by infrared absorption the CO gas extracted and carried by the inert gas stream to successively determine the amount of reacted oxygen; reacted oxygen amount peak detecting means for detecting a peak corresponding to the amount of reacted oxygen from data on the amount of reacted oxygen successively obtained from the reacted oxygen amount measuring means; and inert gas flow rate control means for reducing the flow rate of inert gas stream for each appearance of the peak corresponding to the amount of reacted oxygen detected by the reacted oxygen amount peak detecting means.

(9) An oxygen analyzer for each oxide in an analyte, comprising: analyte heating means for heating an analyte in an inert atmosphere while regulating the temperature rise rate; carbon source feeding means for feeding a carbon source for a reaction with oxygen in the analyte; inert gas stream generating means for generating an inert gas stream for extracting and carrying a CO gas generated as a result of a reaction of oxygen in the analyte with the carbon source; means for measuring the amount of evolved CO gas which measures by infrared absorption the amount of the CO gas extracted and carried by the inert gas stream to successively determine the amount of evolved CO; evolved CO amount peak detecting means for detecting a peak of the amount of evolved CO from data on the amount of evolved CO successively obtained from the evolved CO amount measuring means; inert gas flow rate control means for reducing the flow rate of inert gas stream for each appearance of the peak corresponding to the amount of evolved CO detected by the evolved CO amount peak detecting means; and reacted oxygen amount calculating means for determining the amount of reacted oxygen from the data on the amount of evolved CO.

(10) An analyzer for an oxide in an analyte, comprising: analyte heating means for heating an analyte in an inert atmosphere while regulating the temperature rise rate; carbon source feeding means for feeding a carbon source for a reaction with oxygen in the analyte; inert gas stream generating means for generating an inert gas stream for extracting and carrying a CO gas generated as a result of a reaction of oxygen in the analyte with the carbon source; means for measuring the amount of reacted oxygen which analyzes by infrared absorption the CO gas extracted and carried by the inert gas stream to successively determine the amount of reacted oxygen; reacted oxygen amount peak detecting means for detecting a peak of the amount of reacted oxygen from data on the amount of reacted oxygen successively obtained from the reacted oxygen amount measuring means; inert gas flow rate control means for reducing the flow rate of inert gas stream for each appearance of the peak corresponding to the amount of reacted oxygen detected by the reacted oxygen amount peak detecting means; and computing means for determining the content of each oxide from data on the amount of reacted oxygen obtained in time sequence from the reacted amount measuring means.

(11) An analyzer for an oxide in an analyte, comprising: analyte heating means for heating an analyte in an inert atmosphere while regulating the temperature rise rate; carbon source feeding means for feeding a carbon source for a reaction with oxygen in the analyte; inert gas stream generating means for generating an inert gas stream for extracting and carrying a CO gas generated as a result of a reaction of oxygen in the analyte with the carbon source; means for measuring the amount of evolved CO gas which measures by infrared absorption the amount of the CO gas extracted and carried by the inert gas stream to successively determine the amount of evolved CO; evolved CO amount peak detecting means for detecting a peak of the amount of evolved CO from data on the amount of evolved CO successively obtained by the evolved CO amount measuring means; inert gas flow rate control means for reducing the flow rate of inert gas stream for each appearance of the peak corresponding to the amount of evolved CO detected by the evolved CO amount peak detecting means; and computing means for determining the content of each oxide from data on the amount of evolved CO obtained in time sequence from the evolved CO amount measuring means.

Without pretreatment of an oxide film as a contaminant formed on the surface of an iron and steel, the present invention can accurately separate oxygen in the iron and steel into surface contaminant oxygen and oxygen in the form of oxide inclusions in the iron and steel. Further, an iron and steel analyte can be analyzed for the oxygen or oxide content for each of oxides, such as oxide inclusions in the iron and steel analyte in a simple, accurate, and rapid manner. Thus, the effect of the present invention is significant. Therefore, the present invention is a very useful invention that can meet the needs of steelmaking and other industries where precise control of the form and amount of oxides and the oxygen content is required.

DESCRIPTION OF THE PREFERRED EMBODIMENTS

Contamination sources of contaminant oxygen on the surface of metals are 1) absorbed oxygen from air, and 2)

oxygen as iron oxides produced as a result of oxidation of the surface of a metal due to an increase in temperature of the surface of the metal in the case where the metal is cut with a saw or ground with a grinder in order to adjust the weight of the metal to a desired one. Investigations using an X-ray electrophotometric analyzer have revealed that the latter iron oxides include $Fe_2O_3$, $Fe_3O_4$, and FeO, although the type and amount of the oxides vary depending upon cutting or grinding temperature, time and the like.

Figure 1:
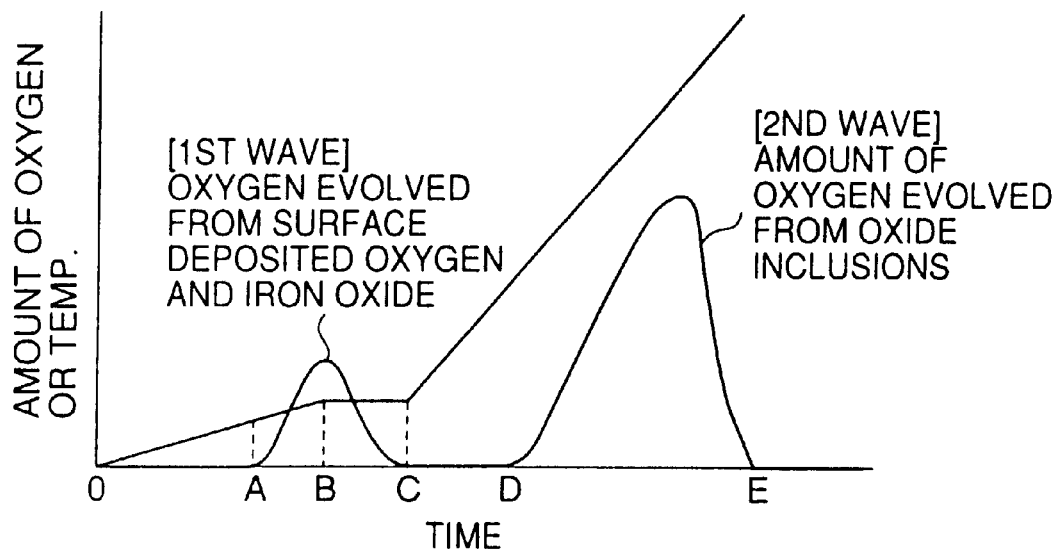
FIG. 1 is an explanatory view showing an extraction curve for oxygen extracted for each oxide according to an example of the present invention.

In the analysis of a metal for oxygen content by inert gas carrying fusion/infrared absorption, it is considered that the reaction MO+C=M+CO (wherein M represents a metal, O represents oxygen, and C represents carbon) takes place in a graphite crucible. The decomposition temperature of iron oxides varies depending upon the type of the oxide and the partial pressure of CO in the crucible. According to the thermodynamic equilibrium calculation and the results of measurement, the decomposition temperature is approximately in the range of from 400 to 1100° C. On the other hand, the thermodynamically equilibrium temperature of oxide inclusions is generally on higher temperature side as compared with the decomposition temperature of iron oxides. Under some metal heating conditions, however, reduction of oxide inclusions with carbon takes places to evolve CO gas even at such a low temperature that the reduction of iron oxides occurs. An extraction curve for oxygen extracted for each of oxides is shown in FIG. 1. The wave having a first peak is an extraction curve corresponding to the amount of oxygen derived from adsorbed oxygen from air and oxygen evolved from iron oxides, while the wave having a second peak is an extraction curve corresponding to the amount of oxygen evolved from oxide inclusions.

When these two oxygen extraction curves are more clearly separated from each other without overlapping, the amount of adsorbed oxygen from air and oxygen evolved from iron oxides can be more accurately determined separately from the amount of oxygen evolved from oxide inclusions. The requirement for this is described in the above item (1).

Regarding the temperature at which the first wave begins to appear, when the temperature rise rate is excessively high, the first wave is likely to overlap with the second wave, rendering wave separation difficult. When the temperature rise rate until the appearance of the first wave is lower, conditions more close to thermodynamic equilibrium are attained. This is considered to facilitate the confirmation of the appearance temperature of the first wave start point A. However, the temperature rise rate is preferably not more than 20° C./sec from the viewpoint of the efficiency of analysis and easiness of the confirmation of rise time. Continuous heat melting at this temperature rise rate soon permits the amount of CO evolved as a result of reduction of iron oxides and the like with carbon to reach the maximum value. When the amount of CO gas evolved has reached the maximum value, the temperature is kept constant and gas extraction is completed. The reason why the temperature is kept constant in a period from the first peak appearance point B to the first wave end point C is that oxide inclusions are decomposed at a temperature or in a time where the first wave still appears, although this varies depending upon the amount, size, composition, and position of oxide inclusions in the metal.

Subsequently, after the completion of the appearance of the first wave, the analyte may be further heated to rapidly decompose the oxide inclusions to obtain a second wave as an oxygen extraction curve corresponding to the amount of the oxide inclusions.

As described above, without pretreatment of a metal to remove an oxide film as a contaminant formed on the surface of a metal analyte, oxygen in the metal can be separated into surface contaminant oxygen and oxygen contained in the metal in the form of oxide inclusions and hence can be accurately determined for each type of oxygen, by a method for analyzing a metal for oxygen, using inert gas carrying fusion/infrared absorption analysis, comprising the steps of: placing a metal analyte in a graphite crucible; heat-melting the metal analyte; extracting a gas from the melt bath; and analyzing the gas to determine the total oxygen content of the metal in the form of a plurality of separated waves, wherein the metal analyte is heated at a temperature rise rate of not more than 20° C./sec in a period from a starting point A of first wave to a peak appearance point B of the first wave, held at a constant temperature in a period from the peak appearance point B of the first wave to an end point C of the first wave, and, after the completion of the appearance of the first wave, is heated to melt the metal analyte for further analysis. The temperature rise rate in a period from the first wave start point A to the first wave peak appearance point B is suitably not more than 20° C./sec, particularly preferably not more than 5° C./sec. Further, the temperature rise rate after the end of the first wave is not particularly limited. The temperature rise rate is preferably high from the viewpoint of the efficiency of the analysis.

The temperature rise rate in a period from the metal analyte heating start point to the first wave start point A also is not particularly limited. However, if the appearance time or temperature of the first wave appearance start point A, which in some cases varies depending upon the type of the metal analyte, could be experimentally grasped, a higher temperature rise rate is preferred from the viewpoint of the efficiency of the analysis. In general, the appearance temperature of the first wave start point A is in many cases 400° C. or above. Therefore, until the temperature reaches about 400° C., the temperature rise rate may be, for example, not less than 20° C./sec.

Figure 3:
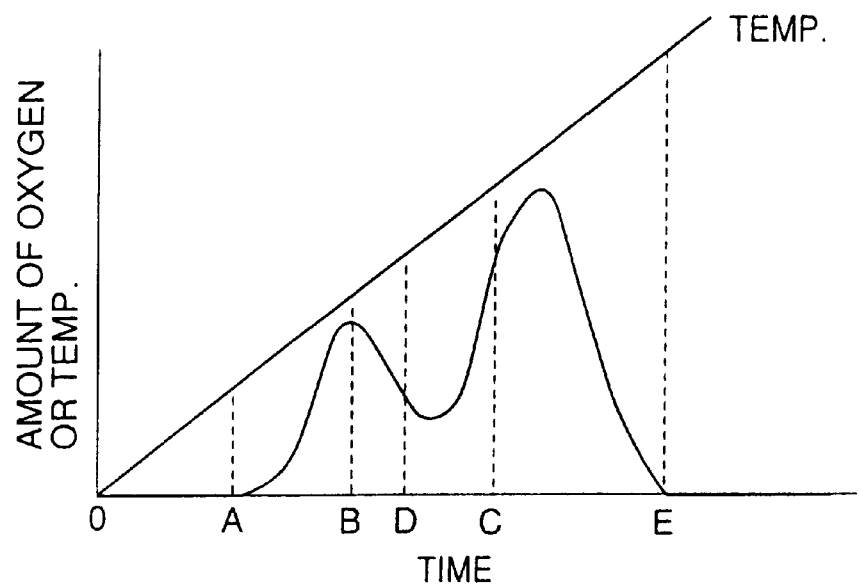
FIG. 3 is an explanatory view showing one example of the appearance of a plurality of extraction curves corresponding respectively to amounts of oxygen.

In FIG. 1 showing an extraction curve for oxygen, the first wave is an extraction curve corresponding to the amount of adsorbed oxygen from air and oxygen evolved from iron oxides, while the second wave is an extraction curve for oxygen corresponding to the amount of oxygen evolved from oxide inclusions. For the first extraction curve corresponding to the amount of adsorbed oxygen from air and oxygen evolved from iron oxides, a plurality of waves in some cases appears, as shown in FIG. 3, depending upon the surface state of the analyte and conditions for the analysis.

When these oxygen extraction curves are more clearly separated from each other without overlapping, the amount of adsorbed oxygen from air and oxygen evolved from iron oxides can be more accurately determined separately from the amount of oxygen evolved from oxide inclusions. The requirement for this is described in the above item (2).

Figure 4:
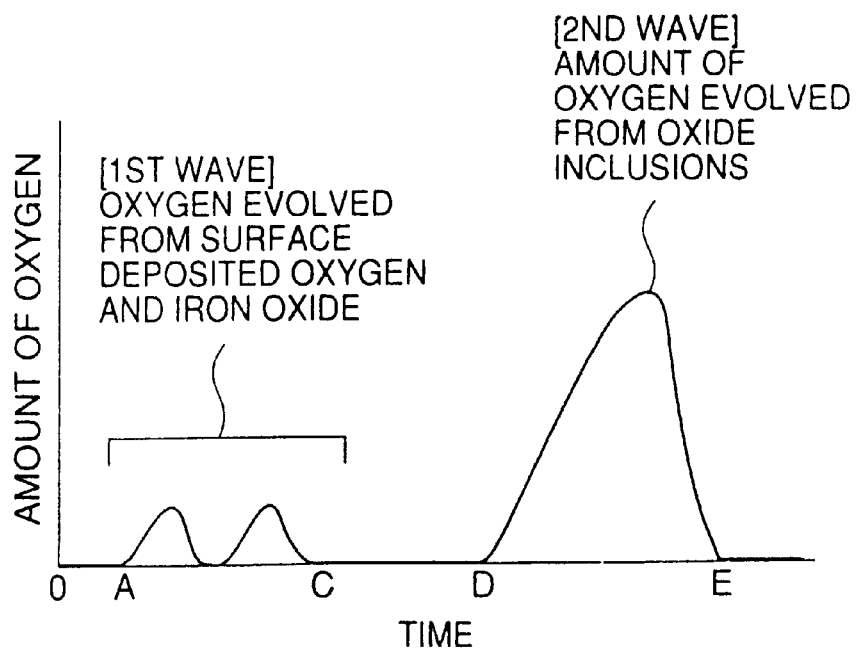
FIG. 4 is an explanatory view showing the form of a first wave, wherein the temperature in the first wave end point C shown in FIG. 1 is below 900° C., in comparison with the form of a first wave, wherein the temperature in the first wave end point C shown in FIG. 1 is 900° C. or above.

FIG. 4 shows a diagram showing an oxygen extraction curve for a first wave, wherein the temperature in the first wave end point C is below 900° C., in comparison with the form of a first wave, wherein the temperature in the first wave end point C is 900° C. or above.

When the temperature of the point C is below 900° C., the amount of oxygen after the point C is on the same level as the back ground before the point A and, thereafter, the second wave appears. On the other hand, when the temperature of the point C is 900° C. or above, for the first wave, the amount of oxygen at the maximum oxygen evolution point, the point B and after the point C is larger than the amount of oxygen evolved in the case where the temperature of the point C is below 900° C. This tendency of an increase in oxygen is more significant when the temperature of the point C is higher. Specifically, when the temperature of the point C is 900° C. or above, a part of oxide inclusions begins to be decomposed causing a part of the amount of oxygen in the second wave to be embraced in the first wave, although the degree of this unfavorable phenomenon varies depending upon the amount, size, composition, position and the like of oxide inclusions in the iron and steel.

According to the present invention, without pretreatment of a metal to remove an oxide film as a contaminant formed on the surface of an iron and steel, oxygen in the iron and steel can be separated into surface contaminant oxygen and oxygen contained in the iron and steel in the form of oxide inclusions and hence can be accurately determined for each type of oxygen, by a method for analyzing an iron and steel for oxygen present in a very small amount, comprising the steps of: placing an iron and steel analyte in a graphite crucible in an inert gas atmosphere; heat-melting the analyte; extracting a CO gas from the melt bath; and analyzing the gas to determine toe oxygen content of the iron and steel in the form of a plurality of separated wages, wherein the analyte for an iron and steel is heated so as not to exceed 900° C. in a period from the initiation of heating of the analyte for an iron and steel to the end point of a wave, which has appeared at a temperature below 900° C. and closest to 900° C., and subsequently further heated for analysis.

In the present invention, the method for analysis for gas or oxygen is not particularly limited so far as the method comprises placing a metal analyte in a graphite crucible in an inert gas atmosphere, heat-melting the metal analyte, and extracting CO gas from the melt bath. A typical method is the so-called "inert gas carrying fusion/infrared absorption method." Further, according to studies conducted by the present inventor, oxygen derived from oxide inclusions is extracted in a temperature region of 900° C. or above, and CO gas evolved in a temperature region of below 900° C. is regarded as one derived from contaminant oxygen, such as adsorbed oxygen on the surface of the metal analyte and iron oxide coating on the surface of the metal analyte. Based on the above finding, in the present invention, the wave of the extraction curve for gas evolved at a temperature of below 900° C. is not particularly taken into consideration, and waves of gas extraction curves for CO gas evolved at a temperature of 900° C. or above are adopted for analysis for each oxide inclusion.

For example, there are various oxide inclusions, such as $Al_2O_3$, $SiO_2$, CaO, MgO, and MnO, in iron and steel materials. These oxide inclusions are present in various forms, such as single forms and composite forms including $MgO \cdot Al_2O_3$.

The decomposition temperature of the oxide varies depending upon the type of oxide and the partial pressure of CO within the crucible. The reaction temperature may be estimated or determined by thermodynamic equilibrium calculation or based on the results of measurement. The present inventor has found that, in analysis by the inert gas carrying fusion/infrared absorption method or the like, the decomposition temperature of the oxide is greatly influenced by analyte heating conditions, independently of the type of the oxide. Specifically, the reaction temperature approaches the equilibrium calculation value with reducing the temperature rise rate, leading to better separability of gas extraction curves for respective oxides. On the other hand, increasing the temperature rise rate deteriorates the separability of gas extraction curves for respective oxides.

Figure 5:
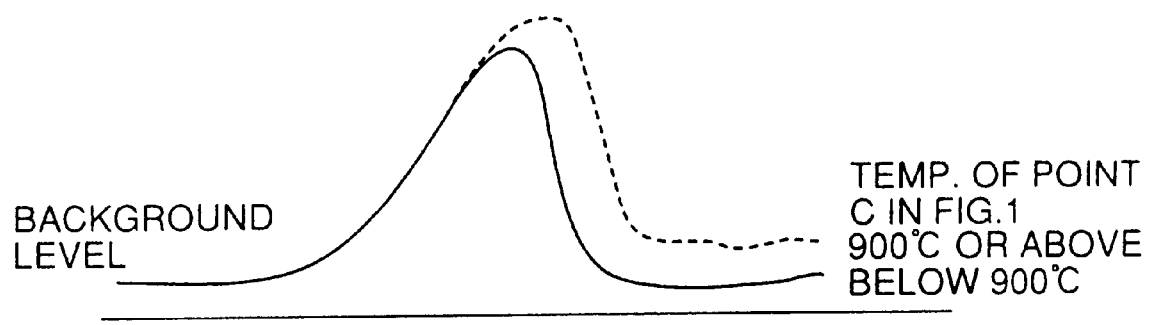
FIG. 5 is an explanatory view showing an extraction curve for oxygen according to Examples 8 to 10 of the present invention.

In the present invention, this finding is applied to gas analysis of a metal analyte for each oxide inclusion. One example of a gas extraction curve obtained according to the method of the present invention is shown in FIG. 5. For example, when n types of oxide inclusions are contained in the analyte, a first peak, a second peak, . . . an nth peak are obtained in the order of reducibility of oxides.

When these oxygen extraction curves are more clearly separated from each other without overlapping, determination can be carried out more accurately for each oxide. The requirement for this is described in the above item (3).

When the metal analyte containing a very small amount of oxygen is analyzed by the inert gas carrying fusion/infrared absorption method or the like, the influence of the proportion of the amount of the surface contaminant oxygen in the total amount of oxygen is not negligible. Therefore, analysis is carried out after the surface of the metal is polished by electrolytic polishing or chemical polishing to remove surface contaminant oxygen. In this method, the influence of surface contamination cannot be completely eliminated. Iron oxides or hydroxides constituting the surface contaminant layer, such as FeO, $Fe_3O_4$, and FeOOH, can be decomposed at a relatively low temperature at the temperature rise rate of the analyte at the time of analysis for oxygen. This is the reason why contaminant oxygen on the surface of the metal is separated and removed at a temperature of below 900° C. before the analysis for the content of oxygen as oxide inclusions, and oxygen attributable only to oxide inclusions is extracted and determined at a temperature of 900° C. or above.

Regarding the temperature at which each peak appears, when the temperature rise rate is excessively high, the reaction temperature range for the first oxide approaches the reaction temperature range for the second oxide, making it difficult to separate waves from each other. When the temperature rise rate is lower, conditions more close to thermodynamic equilibrium are attained. However, a temperature rise rate of not more than 2° C./sec is necessary for analysis for each oxide from the viewpoint of working efficiency and easiness of the confirmation of the appearance temperature of the wave start point. Continuous heat melting at this temperature rise rate soon permits the amount of CO gas evolved as a result of reduction of oxide inclusions in the analyte with carbon to reach the maximum value. When the amount of CO gas evolved has reached the maximum value, the temperature is kept constant and gas extraction is completed. The reason why the temperature is kept constant in a period from each wave peak appearance point $B_n$ to each wave end point $C_n$ is that continuous heating during this period causes (n+1)th oxide inclusion to be decomposed at a temperature or in a time where the nth wave still appears, although this varies depending upon the amount, size, composition, and position of other inclusions in the analyte.

Subsequently, after the completion of the appearance of the nth wave, the analyte is further heated to obtain a second wave as a gas extraction curve corresponding to the amount of the (n+1)th oxide inclusion.

This heating method is repeated, and, finally, at the end of the analysis, n waves extracted from n oxide inclusions present in the analyte are obtained. When the position of the wave appearance for each of artificially prepared oxides is previously confirmed, the oxide inclusion in the analyte can he identified from the waves. Further, the amount of oxygen for each oxide inclusion in the analyte can be determined from the waves.

The method for heating to 900° C. is not particularly limited. Also for the heating to 900° C., however, the temperature rise rate is preferably not more than 2° C./sec from the viewpoint of avoiding the adverse effect on the whole analysis.

Further, the present invention is based on a technique wherein an analyte is heated in an inert atmosphere to react the analyte with a carbon source, and CO gas evolved as a result of the reaction of oxygen in the analyte with the carbon source is extracted into an inert gas stream and analyzed by the infrared absorption method to determine the amount of reacted oxygen. Although the carbon source is not particularly limited, graphite crucibles, graphite powders, graphite capsules, carbon contained in the analyte and the like may be used as the carbon source.

Among others, a practically useful method is such that a graphite crucible is provided as the carbon source and the analyte is placed in the graphite crucible and heat-melted to evolve CO gas. It is also possible to use a method wherein a graphite powder is provided as the carbon source and is mixed with the analyte and the mixture is then heated.

One of the characteristic features of the present invention resides in that, based on the above technique, the analyte is reacted with the carbon source while regulating the temperature rise rate of the analyte, successively evolved CO gas is extracted into an inert gas stream, and the CO gas is successively analyzed to determine the amount of reacted oxygen or the amount of evolved CO to accumulate data on the amount of reacted oxygen or data on the amount of evolved CO in time sequence. The amount of oxygen or oxide for each of oxides can be calculated from the successively obtained data on the amount of reacted oxygen or data on the amount of evolved CO.

Specifically, it is considered that the oxide in the analyte is reacted with the carbon source as follows: MO+C=M+CO (wherein M represents a metal, O represents oxygen, and C represents carbon). In this connection, the present inventor has found that, since the reaction temperature varies from oxide to oxide, reacting the oxide with the carbon source by heating while closely controlling the temperature rise rate of the analyte enables the reaction to take place in a different time for each oxide and, consequently, CO gas to be extracted in a different time for each oxide. According to this method, CO gas extracted in each time is carried by an inert gas stream and successively analyzed and determined to calculate the amount of oxygen derived from the oxide reacted in a certain time or the amount of the oxide reacted in the certain time.

Means for calculating or computing the amount of oxygen or the amount of oxide for each of oxides can be classified roughly into a method wherein data on the amount of reacted oxygen are accumulated in time sequence and the amount of oxygen or oxide is determined based on the data accumulated in time sequence and a method wherein data on evolved CO are accumulated in time sequence and the amount of oxygen or oxide is determined based on the data accumulated in time sequence.

In the method for determining the amount of oxygen or oxide based on the data on the amount of reacted oxygen accumulated in time sequence, data during the reaction time corresponding to the reaction timing for each of oxides (appearance time of each wave according to the following method wherein the reaction timing is expressed in terms of a wave) are integrated to determine the amount of oxygen or the amount of oxide for each of oxides. Further, data on reacted oxygen are successively accumulated, and the total amount of oxygen or oxide is calculated.

In the method for determining the amount of oxygen or oxide based on the data on the amount of evolved CO accumulated in time sequence, data during the reaction time corresponding to the reaction timing or each of oxides (appearance time of each oxide according to the following method wherein the reaction timing is expressed in terms of a wave) are integrated, and the amount of oxygen or the amount of oxide may be calculated from the obtained amount of CO gas evolved by the reduction reaction for each oxide. Further, data on reacted CO are successively accumulated, and the total amount of oxide or the total amount of oxygen is calculated.

Figure 11:
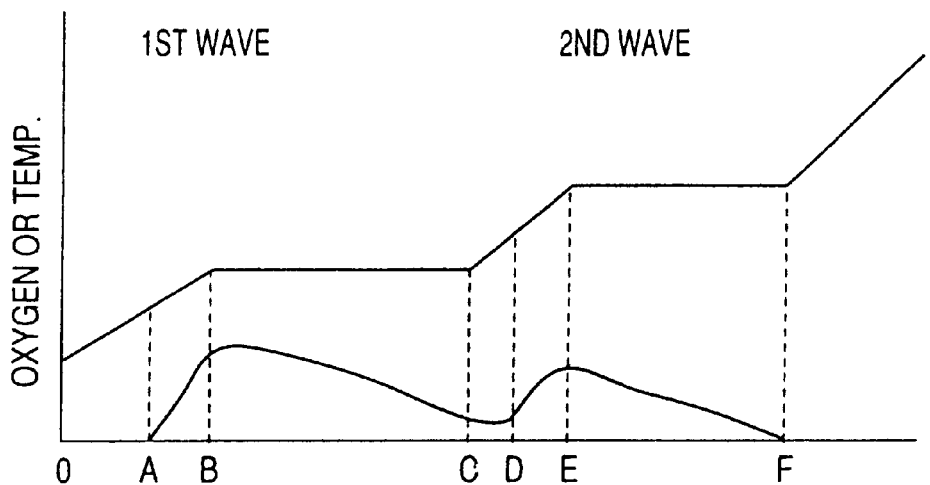
FIG. 11 is an explanatory view showing a curve for the amount of extracted oxygen in time sequence for each of oxide inclusions obtained using the method and apparatus according to the present invention.

One example of a graph showing the amount of extracted oxygen (corresponding to the amount of extracted CO gas) in time sequence obtained using the method and apparatus according to a working example of the present invention is shown in FIG. 11. For example, when n types of oxides are contained in the analyte, waves having n peaks, that is, a wave having a first peak, a wave having a second peak, ... a wave having an nth peak, are obtained in the order of reducibility of oxides.

The regulation of the temperature rise rate of the analyte is specifically carried out as follows. The analyte is gradually heated, held at a constant temperature in a period from the appearance of a first peak for the amount of extracted oxygen or extracted CO gas to the end of the first wave, gradually heated in a period from the end of the first wave to the appearance of a second peak, held at a constant temperature from the appearance of the second peak to the end of the second wave, gradually heated in a period from the end of the second wave to the appearance of a third peak, held at a constant temperature in a period from the appearance of the third peak to the end of the third wave, and gradually heated in a period from the end of the third wave to the appearance of a fourth peak. Thus, a repetitive pattern of rising of temperature and holding at a constant temperature is preferred.

More specifically, for example, in the case of the analysis of a bearing steel containing four oxide inclusions, the analyte is heated at a temperature rise rate of 1° C./sec in a period from the analyte heating start point to the first wave peak appearance point, at a temperature rise rate of 0° C./sec in a period from the first wave peak appearance point to the end point of the first wave, again at a temperature rise rate of 1° C./sec in a period from the end point of the first wave to a second peak appearance point, at a temperature rise rate of 0° C./sec in a period form the second peak appearance point to the end point of the second wave, at a temperature rise rate of 1° C./sec in a period from the end point of the second wave to a third peak appearance point, at a temperature rise rate of 0° C./sec in a period from the third peak appearance point to the end point of the third wave, again at a temperature rise rate of 1° C./sec in a period from the end point of the third wage to a fourth peak appearance point, at a temperature rise rate of 0° C./sec in a period from the fourth peak appearance point to the end point of the fourth wave, and again at temperature rise rate of 1° C./sec in a period from the end point of the fourth wave to the completion of the analysis. The above control operation provides four peaks corresponding respectively to the four inclusions.

Regarding the temperature at which each peak appears, when the temperature rise rate is excessively high, the reaction temperature range for the first oxide approaches the reaction temperature range for the second oxide, making it difficult to separate waves from each other. A lower temperature rise rate is considered to permit conditions more close to thermodynamic equilibrium to be attained. An excessively low temperature rise rate results in deteriorated efficiency of the analysis and hence is unsuitable for the analysis of practically used steels. For this reason, it is recommended that the temperature rise rate of the analyte is not more than 0.01 to 20° C./sec.

The type of the oxide contemplated in the present invention is not limited, and examples thereof include $Al_2O_3$, $SiO_2$, CaO, MgO, MnO, $Cr_2O_3$, and $TiO_2$ and inclusions of composite oxides of these oxides. In the case of iron and steel materials as representative analytes contemplated in the present invention, oxides inclusions in the iron and steel materials include various oxides, such as $Al_2O_3$, $SiO_2$, CaO, MgO, and MnO. These oxide inclusions are present in various forms, such as single forms and composite forms including $MgO \cdot Al_2O_3$.

Another characteristic feature of the present inventions resides in that, while controlling the temperature rise rate of the analyte as described above, successively extracted CO gas is successively analyzed to determine the amount of reacted oxygen or the amount of evolved CO, a peak of the amount of reacted oxygen or the amount of evolved CO is detected from successively obtained data on the amount of reacted oxygen or data on the amount of evolved CO, and the analysis is carried out while reducing the flow rate of an inert gas stream, which extracts CO gas, for each appearance of the detected peak corresponding to the amount of reacted oxygen or the amount of evolved CO.

As described above, the decomposition temperature of the oxide varies depending upon the type of oxide. The present inventor has further found that the decomposition temperature of each oxide is influenced by the partial pressure of the atmosphere in the reaction of each oxide with the carbon source. Further, as a result of studies, as shown in FIG. 12, the relationship between the reaction temperature of each oxide and the partial pressure of CO could be estimated or determined by thermodynamic equilibrium calculation or based on the results of measurements.

Figure 12:
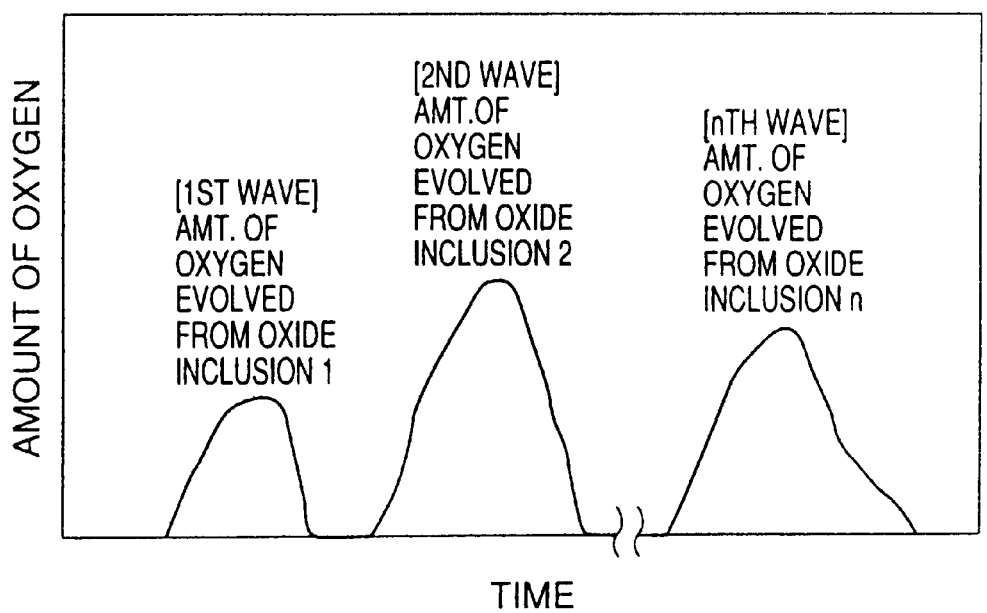
FIG. 12 is a conceptual diagram showing the relationship, between the decomposition temperature for each of oxides and the partial pressure of CO (amount of oxygen constituting oxide), provided by thermodynamic calculation.

As can be seen from an explanatory view, in FIG. 12, showing the relationship between the decomposition temperature for each of oxides and the partial pressure of CO (corresponding to amount of oxygen constituting oxide), the decomposition temperature of the oxide is considered to change according to the partial pressure of CO. Therefore, at some partial pressure of CO under which the oxide is decomposed, different oxides often exhibit the same decomposition temperature. In this case, the waves shown in FIG. 11 is considered to overlap with each other, making it impossible to identify the type of oxide. This may be expressed by the following formula:

$$\Delta G = -RT \ln P_{CO} \qquad (1)$$

wherein $\Delta G$ represents formation free energy of oxide, R represents gas constant, T represents temperature, and $P_{CO}$ represents the partial pressure of CO gas at the time of reduction of oxide with carbon and corresponds to the amount of oxygen for each oxide. When waves of the curve for the amount of extracted oxygen (amount of extracted CO gas) are more clearly separated from each other without overlapping, determination can be carried out more accurately for each oxide.

Based on such finding, the present inventors have thought that means for controlling the partial pressure of CO in the atmosphere at the time of CO gas extraction is necessary for attaining the objects of the present invention. The partial pressure of CO can be expressed by the following formula 2.

$$((\text{amount of CO gas})/(\text{amount of inert gas} + \text{amount of CO gas})) = \text{partial pressure of CO} \qquad (2)$$

In this case, the value of the numerator in the formula 2 is a value that is necessarily determined by the content of oxygen in the analyte. The partial pressure of CO at the time of the analysis can be controlled as desired by varying the amount of the inert gas in the denominator.

Specifically, varying the amount of the inert gas enables the decomposition temperature of each oxide at the time of analysis to be controlled as desired and can significantly improve the separability of waves of CO gas extraction curve for respective oxides from each other or one another.

Thus, the analytical method of the present invention has been developed wherein a peak of the amount of reacted oxygen or the amount of evolved CO is detected from successively obtained data on the amount of reacted oxygen or data on the amount of evolved CO, and the analysis is carried out while reducing the flow rate of an inert gas stream, which extracts CO gas, for each appearance of the detected peak corresponding to the amount of reacted oxygen or the amount of evolved CO.

Coulometry, conductometry, gas chromatography, an infrared absorption method, and a nonaqueous solvent method may be used as means for detecting a peak of the amount of reacted oxygen or the amount of evolved CO from data on the amount of reacted oxygen or data on the amount of evolved CO.

The inert gas flow rate control means for reducing the flow rate of the inert gas stream for extracting CO gas for each appearance of a peak on the detected amount of reacted oxygen or he detected amount of evolved CO may be constructed, for example, so that a flowmeter and an inert gas flow rate control valve are used to permit the flow rate to be controlled as desired.

Further, the flow rate of the inert gas for extracting CO gas is preferably not more than 2000 cc/min. When the flow rate of the inert gas for extracting CO gas exceeds 2000 cc/min, a variation in amount of detected gas is likely to become significant, although this varies depending upon peak detection time. The flow rate of the inert gas, for example, in the case of the apparatus according to an embodiment of the present invention, shown in FIG. 13, may be regulated by gas flow rate controllers 8, 9.

Further, the present inventors have found that the amount of the analyte melted is also important for analysis by the inert gas carrying/infrared absorption method. Specifically, for example, in the case of a metal analyte having a very low oxygen content or an analyte having a low oxygen content and containing many types of oxides, the amount of oxygen evolved from he oxide is very small. This is likely to cause the wave for extracted oxygen to overlap with a noise, inherent in the apparatus, unrelated to the amount of oxygen, making it difficult to determine only the amount of oxygen evolved from oxides in the analyte. In order to prevent this unfavorable phenomenon, the amount of the analyte melted may be increased. However, the amount of the analyte melted is preferably not more than about 5 g from the viewpoint of the efficiency of the analysis and homogeneous melting.

Figure 14:
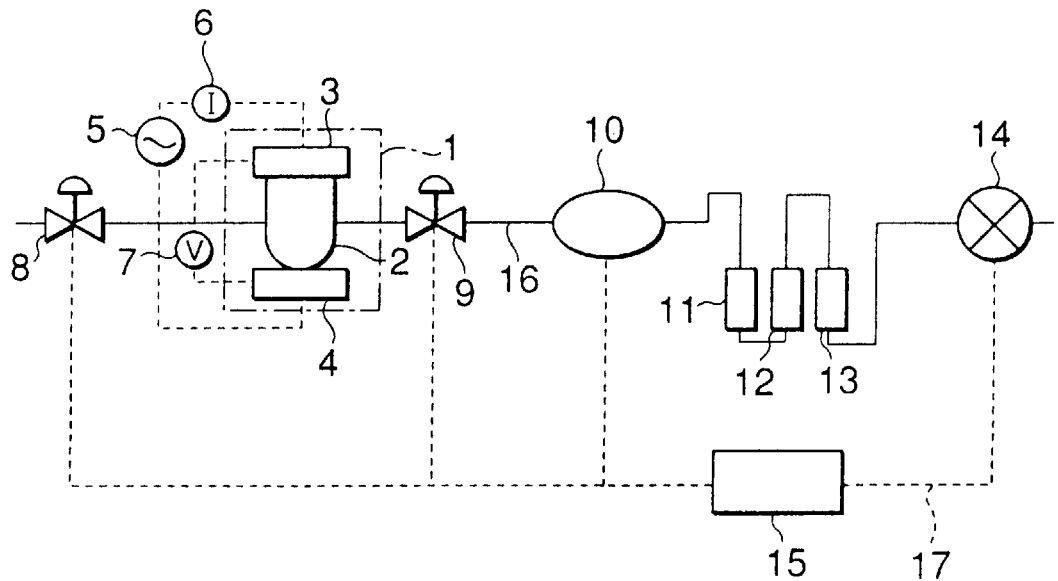
FIG. 14 is a schematic explanatory view showing an infrared CO absorption detector.

As shown in FIG. 14, a reference cell 21 in an infrared CO absorption detecting apparatus 10 is filled with nitrogen or the like not having an infrared absorption capability, and a detector 22 is filled with a high-concentration gas to be determined. The detector 22 is partitioned with a thin partition 23 into two compartments. A metal sheet provided on the partition 23 serves as one pole of a capacitor 24. When the analyte contains a component to be determined, the quantity of light, which enters the detector 22, is decreased by the quantity absorbed by the component. This creates a difference in pressure between both the compartments of the detector 22 to cause displacement of the partition 23, resulting in a change in capacitance of the capacitor 24. The capacitance change may be measured to learn the concentration of the component to be determined.

The sensitivity of the infrared CO absorption detecting apparatus 10 depends upon the difference in quantity of light between the reference cell 21 and the measuring cell 25. The optical path length L of the infrared CO absorption detecting apparatus is important for increasing the difference in quantity of light. When the optical path length L exceeds 50 mm, distinguishment of the extracted wave signal from the noise is difficult, or otherwise normal waves cannot be obtained, although this depends also upon the combination with the intensity of an infrared light source 26. When the optical path length L is excessively short, the difference in quantity of light between the reference cell 21 and the measuring cell 25 is less likely to develop. For this reason, the optical path length L of the infrared CO absorption detecting apparatus according to the present invention is preferably not more than 50 mm.

Infrared CO absorption detecting apparatuses usable in the present invention include those of cross flow type or other various forms or having various structures. The form, structure, type and the like are not particularly limited so far as the above measurement principle is met.

EXAMPLES 1 to 3

Examples 1 to 3 of the present invention, together with Comparative Examples 1 to 3, shown in Table 1 will be described. In each example, the content of oxygen in a metal was determined by an inert gas carrying fusion/infrared absorption method wherein a metal analyte is placed in a graphite crucible, the analyte is heat-melted, and a gas is extracted from the melt bath and analyzed.

Figure 7:
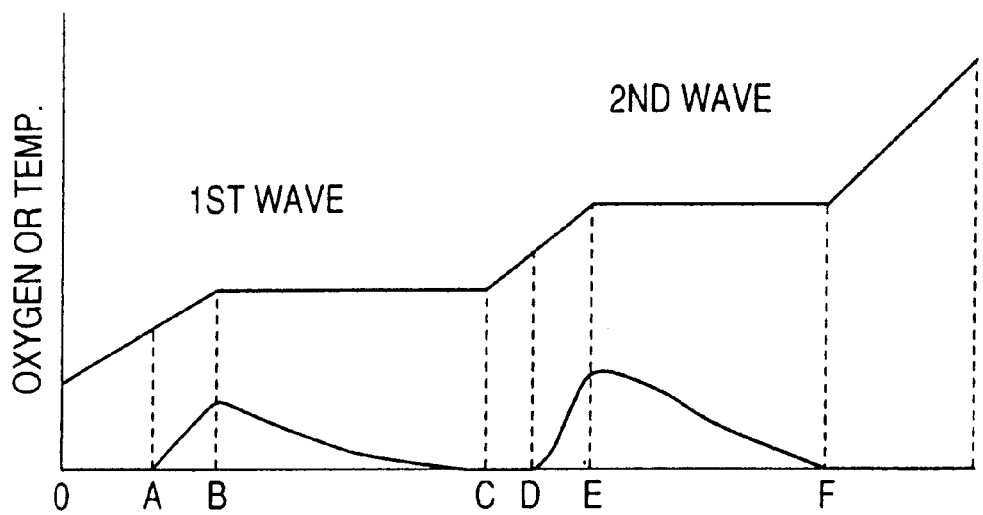
FIG. 7 is an explanatory view showing an extraction curve for oxygen according to Comparative Examples 10 to 12.

For Comparative Example 1, 1 g of a bearing steel analyte was immersed in an $HF-H_2O_2$ solution, and analysis was then carried out in such a manner that, in FIG. 7, the analyte was heated at a temperature rise rate of 30° C./sec in a period from a heating start point 0 to a peak appearance point B of the first wave, at a temperature rise rate of 30° C./sec also in a period from the peak appearance point B of the first wave to an end point C of the first wave, and at a temperature rise rate of 50° C./sec after the end point C of the first wave. It was difficult to separate the first wave corresponding to the amount of oxygen evolved from surface deposited oxygen and iron oxide from the second wave corresponding to the amount of oxygen evolved from oxide inclusions, and the total oxygen content was 4.1 ppm. In Example 1 of the present invention, the same bearing steel as used in Comparative Example 1 was used. In Example 1, 1 g of the bearing steel was analyzed, without the pretreatment, in such a manner that, in FIG. 1, the analyte was heated at a temperature rise rate of 15° C./sec in a period from a heating start point 0 to a peak appearance point B of the first wave, at a temperature rise rate of 0° C./sec in a period from the peak appearance point B of the first wave to an end point C of the first wave, and at a temperature rise rate of 50° C./sec after the end point C of the first wave. The oxygen content corresponding to the first wave was 1.8 ppm, the oxygen content corresponding to the second wave was 3.1 ppm, and the total oxygen content was 4.9 ppm. From the above results, when the content of oxygen in the form of oxide inclusions in the bearing steel in Comparative Example 1 is presumed to be 3.1 ppm, (total oxygen content in Comparative Example 1)—(oxygen content corresponding to the second wave in Example 1)=4.1–3.1=1.0 ppm. Therefore, the oxygen content 1.0 ppm is estimated to be oxygen that has been left without being fully removed by chemical polishing with the $HF-13 H_2O_2$ solution.

In Comparative Example 2, 1 g of a carbon steel for mechanical structures was electrically polished with a non-aqueous solvent electrolyte of a 4% sulfosalicylic acid/1% lithium chloride/methyl alcohol solution under conditions of an electrolysis potential of 1 V, a current of 500 mA, and an electrolysis time of 4 min, and ultrasonically cleaned in a methanol solution for 8 min, followed by analysis for oxygen. The analysis was carried out in such a manner that, in FIG. 7, the analyte was heated at a temperature rise rate of 50° C./sec in a period from a heating start point 0 to a peak appearance point B of the first wave, at a temperature rise rate of 50° C./sec also in a period from the peak appearance point B of the first wave to an end point C of the first wave, and at a temperature rise rate of 60° C./sec after the end point C of the first wave. As with Comparative Example 1, it as difficult to separate the first wave corresponding to the amount of oxygen evolved from surface deposited oxygen and iron oxide from the second wave corresponding to the amount of oxygen evolved from oxide inclusions, and the total oxygen content was 8.4 ppm.

In Example 2 of the present invention, the same carbon steel for mechanical structures as used in Comparative Example 2 was analyzed. In Example 2, the analyte was not pretreated. The analysis was carried out in such a manner that, in FIG. 1, the metal analyte was heated at a temperature rise rate of 10° C./sec in a period from a heating start point 0 to a peak appearance point B of the first wave, at a temperature rise rate of 0° C./sec in a period from the peak appearance point B of the first wave to an end point C of the first wave, and at a temperature rise rate of 70° C./sec after the end point C of the first wave. The oxygen content corresponding to the first wave was 2.5 ppm, the oxygen content corresponding to the second wave was 7.3 ppm, and the total oxygen content was 9.8 ppm. Therefore, as with Comparative Example 1, in Comparative Example 2, the oxygen content 1.1 ppm (8.4–7.3=1.1 ppm) is estimated to be oxygen that has been left without being removed by the electrolytic polishing. Thus, it was difficult to completely remove contaminants, such as an oxide film, formed on the surface of the analyte, by various pretreatments before the analysis. Even when identical treatment was used, the total oxygen content was not identical and a variation in found values occurred.

Figure 2:
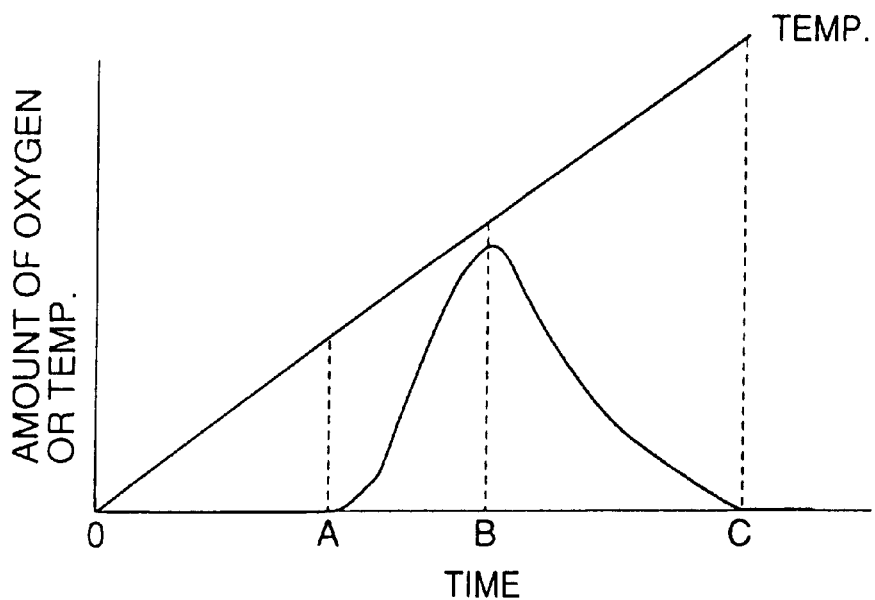
FIG. 2 is an explanatory view showing an extraction curve for oxygen according to a comparative example, wherein first and second waves fully overlap with each other with separation.

In Comparative Example 3, the bearing steel was analyzed, without pretreatment, that is, chemical polishing in Comparative Example 1 and electrolytic polishing in Comparative Example 2, in such a manner that, in FIG. 1, the analyte was heated at a temperature rise rate of 50° C./sec in a period from a heating start point 0 to a peak appearance point B of the first wave, at a temperature rise rate of 50° C./sec in a period from the peak appearance point B of the first wave to an end point C of the first wave, and at a temperature rise rate of 50° C./sec after the end point C of the first wave. As shown in FIG. 2, the first wave corresponding to the amount of oxygen evolved from surface deposited oxygen and iron oxide and the second wave corresponding to the amount of oxygen evolved from oxide inclusions could not be separated from each other and completely mutually overlapped. In Example 3, the same bearing steel as used in Comparative Example 3 was used.

In Example 3, 1 g of the bearing steel analyte was analyzed, without the pretreatment, in such a manner that, in FIG. 1, the analyte was heated at a temperature rise rate of 5° C./sec in a period from a heating start point 0 to a peak appearance point B of the first wave, at a temperature rise rate of 0° C./sec in a period from the peak appearance point B of the first wave to an end point C of the first wave, and at a temperature rise rate of 100° C./sec after the end point C of the first wave. The oxygen content corresponding to the first wave was 2.3 ppm, the oxygen content corresponding to the second wave was 2.2 ppm, and the total oxygen content was 4.5 ppm. From the above results, when the content of oxygen in the form of oxide inclusions in the bearing steel in Comparative Example 3 is presumed to be 2.2 ppm, (total oxygen content in Comparative Example 3)−(oxygen content corresponding to the second wave in Example 3)=4.9−2.2=2.7 ppm. Therefore, the oxygen content 2.7 ppm is considered to correspond to the content of oxygen evolved from surface deposited oxygen or iron oxide.

Examples 1 to 3 are examples of the present invention. In Examples 1 to 3, the first wave corresponding to the amount of oxygen evolved from surface deposited oxygen and iron oxide could be clearly separated from the second wave corresponding to the amount of oxygen evolved from oxide inclusions. The experiment was repeated for several steels of the same type. As a result, a variation in found values hardly occurred.

As described above, according to the analytical method of the present invention, without pretreatment of the analyte, such as chemical polishing or electrolytic polishing, contaminant oxygen derived from surface deposited oxygen of the metal and oxygen evolved from iron oxide and oxygen evolved from oxide inclusions could be clearly separated from each other and quantitatively accurately determined.

EXAMPLES 4 to 7

Examples 4 to 7 of the present invention, together with Comparative Examples 4 to 9, shown in Tables 2 and 3 will be described. In all the examples and comparative examples, the content of oxygen in an iron and steel was determined by an inert gas carrying fusion/infrared absorption method wherein an iron and steel analyte is placed in a graphite crucible, the analyte is heat-melted, and a CO gas is extracted from the melt bath and analyzed. At the outset, Comparative Examples 4 to 6 and Examples 4 and 5 shown in Table 2 will be described.

Comparative Example 4 shows the results of the analysis of 1 g of a bearing steel analyte for oxygen wherein the temperature of the point C shown in FIG. 1 was 950° C. The oxygen content corresponding to the first wave was 2.0 ppm, and the oxygen content corresponding to the second wave was 2.9 ppm. Comparative Example 5 shows the results of the analysis of 1 g of a bearing steel analyte for oxygen wherein the temperature of the point C shown in FIG. 1 was 1000° C. The oxygen content corresponding to the first wave was 2.2 ppm, and the oxygen content corresponding to the second wave was 2.7 ppm. Comparative Example 6 shows the results of the analysis of 1 g of a bearing steel analyte for oxygen wherein the temperature of the point C shown in FIG. 1 was 1100° C. The oxygen content corresponding to the first wave was 2.4 ppm, and the oxygen content corresponding to the second wave was 2.5 ppm. Example 4 shows the results of the analysis of 1 g of a bearing steel analyte for oxygen wherein the temperature of the point C shown in FIG. 1 was 890° C. The oxygen content corresponding to the first wave was 1.8 ppm, and the oxygen content corresponding to the second wave was 3.1 ppm. Example 5 shows the results of the analysis of 1 g of a bearing steel analyte for oxygen wherein the temperature of the point C shown in FIG. 1 was 750° C. The oxygen content corresponding to the

TABLE 1

| | Items | Comp.Ex. 1 | Comp.Ex. 2 | Comp.Ex. 3 | Ex. 1 | Ex. 2 | Ex. 3 |
|---|---|---|---|---|---|---|---|
| Pretreatment of analyte | | Done | Done | None | None | None | None |
| Pretreating agent or pretreatment method | | Chemical polishing (HF—$H_2O_2$) | Electrolytic polishing | | | | |
| Temp. rise rate, ° C./sec | Temp. rise rate in period from analyte heating start point 0 to 1st wave start point A | 30 | 50 | 50 | 15 | 10 | 5 |
| | Temp. rise rate in period from 1st wave start point A to 1st wave peak appearance point B | 30 | 50 | 50 | 15 | 10 | 5 |
| | Temp. rise rate in period from 1st wave peak appearance point B to 1st wave end point C | 30 | 50 | 50 | 0 | 0 | 0 |
| | Temp. rise rate after 1st wave end point C | 50 | 60 | 50 | 50 | 70 | 100 |
| Number of waves | | 1. (Impossible to separate 1st wave from 2nd wave) | 1. (Impossible to separate 1st wave from 2nd wave) | 2. (1st wave overlapped with 2nd wave) | 2 | 2 | 2 |
| Total oxygen content, ppm | 1st wave | (4.1) | (8.4) | (4.9) | 1.8 | 2.5 | 2.3 |
| | 2nd wave | | | | 3.1 | 7.3 | 2.2 |
| Steel species | | Bearing steel | Carbon steel for mechanical structure | Bearing steel | Bearing steel | Carbon steel for mechanical structure | Bearing steel | first wave was 1.8 ppm, and the oxygen content corresponding to the second wave was 3.1 ppm. That is, these values were the same as the values obtained in Example 4. As is apparent from the above results, for Comparative Examples 4, 5 and 6 and Examples 4 and 5, the total oxygen content obtained by adding the oxygen content corresponding to the first wave to the oxygen content corresponding to the second wave was identical. However, the oxygen content corresponding to the first wave increased with increasing the temperature of the point C. From this, it is considered that a part of oxygen evolved by decomposition of oxide inclusions, which should appear in the second wave, has been included in the first wave.

Next, Comparative Examples 7 to 9 and Examples 6 and 7 shown in Table 3 will be described. Comparative Example 7 shows the results of the oxygen analysis of 1 g of a carbon steel analyte for a mechanical structure wherein the temperature of the point C shown in FIG. 1 was 950° C. The oxygen content corresponding to the first wave was 2.7 ppm, and the oxygen content corresponding to the second wave was 7.1 ppm. Comparative Example 8 shows the results of the oxygen analysis of 1 g of a carbon steel analyte for a mechanical structure wherein the temperature of the point C shown in FIG. 1 was 1000° C. The oxygen content corresponding to the first wave was 2.9 ppm, and the oxygen content corresponding to the second wave was 6.9 ppm. Comparative Example 9 shows the results of the oxygen analysis of 1 g of a carbon steel analyte for a mechanical structure wherein the temperature of the point C shown in FIG. 1 was 1100° C. The oxygen content corresponding to the first wave was 3.3 ppm, and the oxygen content corresponding to the second wave was 6.5 ppm. Example 6 shows the results of the oxygen analysis of 1 g of a carbon steel analyte for a mechanical structure wherein the temperature of the point C shown in FIG. 1 was 890° C. The oxygen content corresponding to the first wave was 2.5 ppm, and the oxygen content corresponding to the second wave was 7.3 ppm. Example 7 shows the results of the oxygen analysis of 1 g of a carbon steel analyte for a mechanical structure wherein the temperature of the point C shown in FIG. 1 was 750° C. The oxygen content corresponding to the first wave was 2.5 ppm, and the oxygen content corresponding to the second wave was 7.3 ppm. That is, these values were the same as the values obtained in Example 6. As is apparent from the above results, for Comparative Examples 7, 8 and 9 and Examples 6 and 7, the total oxygen content obtained by adding the oxygen content corresponding to the first wave to the oxygen content corresponding to the second wave was identical. However, the oxygen content corresponding to the first wave increased with increasing the temperature of the point C of the comparative example. From this, it is considered that a part of oxygen evolved by decomposition of oxide inclusions, which should appear in the second wave, has been included in the first wave.

For both the bearing steel and the carbon steel for a mechanical structure, even when the temperature of the point C was 750° C. or below, the results were substantially the same as those in Examples 4 to 7. The temperature of the point C is preferably 800 to less than 900° C. from the viewpoint of the efficiency of analysis.

As described above, according to the analytical method according to the examples of the present invention, without pretreatment of the analyte, such as chemical polishing or electrolytic polishing, contaminant oxygen derived from surface deposited oxygen of the iron and steel and oxygen evolved from iron oxide and oxygen evolved for oxide inclusions could be clearly separated from each other and quantitatively accurately determined.

TABLE 2

Steel species: bearing steel

| Items | Comp. Ex. 4 | Comp. Ex. 5 | Comp. Ex. 6 | Ex. 4 | Ex. 5 |
|---|---|---|---|---|---|
| Point C termination temp., ° C. Total oxygen content (ppm) | 950 | 1000 | 1100 | 890 | 750 |
| 1st wave | 2.0 | 2.2 | 2.4 | 1.8 | 1.8 |
| 2nd wave | 2.9 | 2.7 | 2.5 | 3.1 | 3.1 |

TABLE 3

Steel species: Carbon steel for mechanical structure

| Items | Comp. Ex. 7 | Comp. Ex. 8 | Comp. Ex. 9 | Ex. 6 | Ex. 7 |
|---|---|---|---|---|---|
| Point C termination Total oxygen content (ppm) | 950 | 1000 | 1100 | 890 | 750 |
| 1st wave | 2.7 | 2.9 | 3.3 | 2.5 | 2.5 |
| 2nd wave | 7.1 | 6.9 | 6.5 | 7.3 | 7.3 |

EXAMPLES 8 to 10

Examples 8 to 10 of the present invention, together with Comparative Examples 10 to 13, shown in Table 4 will be described. In each example, the content of oxygen in a metal was determined by an inert gas carrying fusion/infrared absorption method wherein a metal analyte is placed in a graphite crucible in an inert gas atmosphere, the analyte is heat-melted, and a CO gas is extracted from the melt bath and analyzed.

Figure 6:
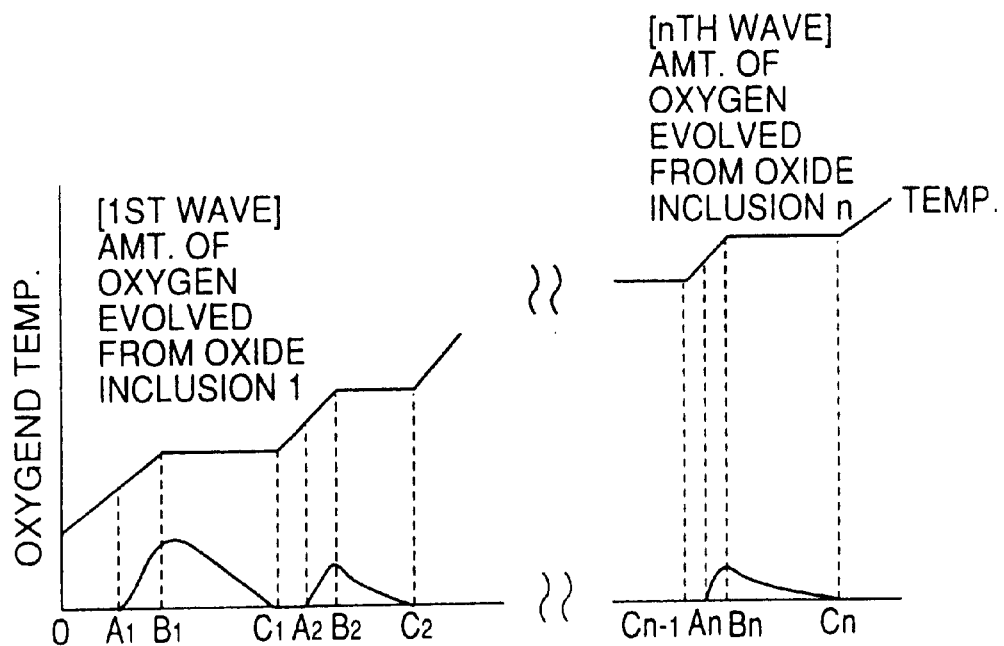
FIG. 6 is an explanatory view showing an extraction curve for oxygen according to Example 8 of the present invention.

In Comparative Example 10, a carbon steel for a mechanical structure was analyzed. As shown in FIG. 7, the analysis was carried out in such a manner that the temperature rise rate of the metal analyte from the initiation of heating to the completion of the analysis was 1° C./sec. It was difficult to separate peaks for respective oxides, and the total oxygen content was 12.1 ppm. In Example 8 of the present invention, the same carbon steel for a mechanical structure as used in Comparative Example 10 was analyzed. As shown in FIG. 6, the analysis was carried out in such a manner that the metal analyte was heated at a temperature rise rate of 1° C./sec in a period from a heating start point 0 to a first wave peak appearance point B and at a temperature rise rate of 0° C./sec in a period from the first wave appearance point B to a first wave end point C. Subsequently, the analyte was heated again at a temperature rise rate of 1° C./sec in a period from the first wave end point C to a second peak appearance point E and at a temperature rise rate of 0° C./sec in a period from the second wave peak appearance point E to the second wave end point F.

Further, the analyte was heated again at a temperature rise rate of 1° C./sec after the second wave end point. In this case, no gas extraction was observed until the analysis was completed. The oxygen content corresponding to the first wave was 1.8 ppm, the oxygen content corresponding to the second wave was 10.3 ppm, and the total oxygen content was 12.1 ppm. Oxides reacted at these respective temperatures were determined by equilibrium calculation. As a result, it was found that the first wave represents $SiO_2$ and the second wave represents $Al_2O_3$. This was in agreement with the results obtained from investigation of the proportions of ingredients constituting the oxides by means of X-ray microanalyzer.

Figure 8:
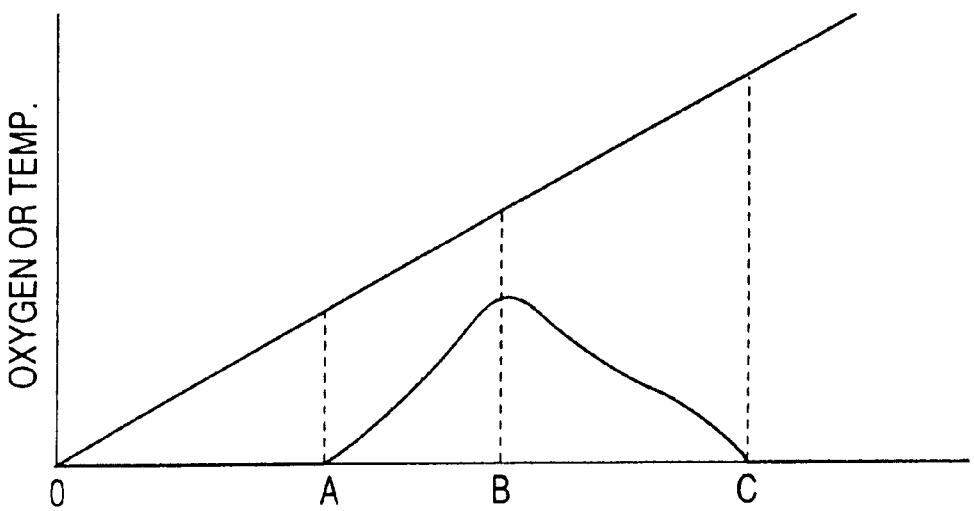
FIG. 8 is an explanatory view showing an extraction curve for oxygen according to Example 9 of the present invention.

In Comparative Example 11, a bearing steel was analyzed. As shown in FIG. 7, the analysis was carried out in such a manner that the analyte was heated at a rate of 1° C./sec in a period from the initiation of heating of the analyte to the completion of the analysis. It was difficult to separate peaks for respective oxides from each other, and the total oxygen content was 3.8 ppm. In Example 9, the same bearing steel as used in Comparative Example 11 was analyzed. As shown in FIG. 8, the analysis was carried out in such a manner that the analyte was heated at a temperature rise rate of 1° C./sec in a period from a heating start point 0 to a first wave peak appearance point B and at a temperature rise rate of 0° C./sec in a period from the first wave appearance point B to a first wave end point C. Subsequently, the analyte was heated again at a temperature rise rate of 1° C./sec in a period from the first wave end point C to a second peak appearance point E and at a temperature rise rate of 0° C./sec in a period from the second wave peak appearance point E to the second wave end point F.

Further, the analyte was heated again at a temperature rise rate of 1° C./sec from the second wave end point F, at a temperature rise rate of 0° C./sec from a third peak appearance point H, and again at a temperature rise rate of 1° C./sec from the third wave end point I. After that, no gas extraction was observed until the analysis was completed. The oxygen content corresponding to the first wave was 1.1 ppm, the oxygen content corresponding to the second wave was 1.4 ppm, the oxygen content corresponding to the third wave was 1.3 ppm, and the total oxygen content was 3.8 ppm. Oxides reacted at these respective temperatures were determined by equilibrium calculation. As a result, it was found that the first wave represents $SiO_2$, the second wave represents $Al_2O_3$, and the third wave represents CaO. This was in agreement with the results obtained from investigation of the proportions of ingredients constituting the oxides by means of X-ray microanalyzer.

Figure 9:
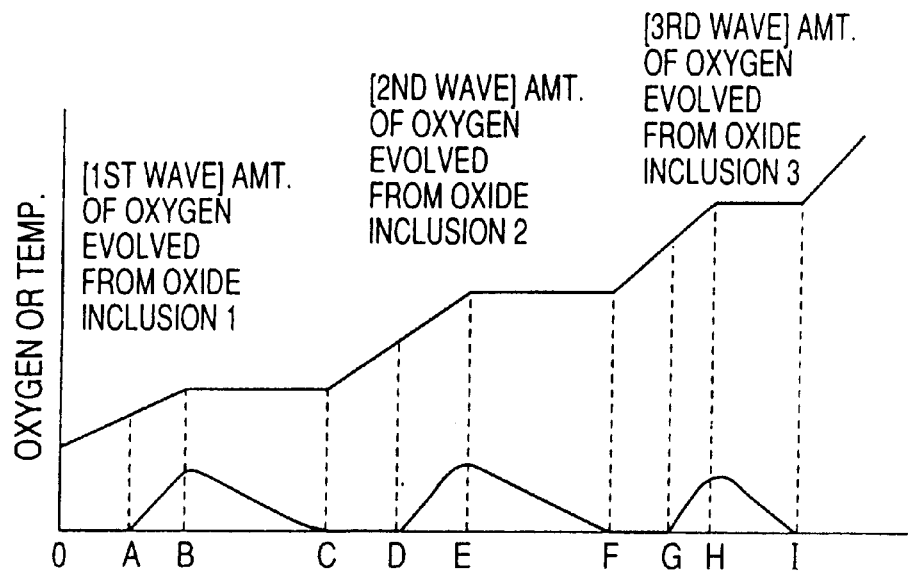
FIG. 9 is an explanatory view showing an extraction curve for oxygen according to Example 10 of the present invention.

In Comparative Example 12, a bearing steel, which is different in steel species from the bearing steel used in Comparative Example 11, was analyzed. The analysis was carried out in such a manner that the analyte was heated at a temperature rise rate of 1° C./sec in a period from the initiation of the analysis to the completion of the analysis. As a result, as shown in FIG. 7, it was difficult to separate wave from each other, and the total oxygen content was 3.9 ppm. In Example 10, the same bearing steel as used in Comparative Example 12 was analyzed. As shown in FIG. 9, the analysis was carried out in such a manner that the analysis was carried out in such a manner that the analyte was heated at a temperature rise rate of 1° C./sec in a period from a heating start point 0 to a first wave peak appearance point B and at a temperature rise rate of 0° C./sec in a period from the first wave appearance point B to a first wave end point C. Subsequently, the analyte was heated again at a temperature rise rate of 1° C./sec in a period from the first wave end point C to a second peak appearance point E and at a temperature rise rate of 0° C./sec in a period from the second wave peak appearance point E to the second wave end point F. Next, the analyte was heated again at a temperature rise rate of 1° C./sec in a period from the second wave end point F to a third wave peak appearance point H, at a temperature rise rate of 0° C./sec in a period from the third wave appearance point H to a third wave end point I, again at a temperature rise rate of 1° C./sec from the third wave end pint I, at a temperature rise rate of 0° C./sec from a fourth wave peak appearance point K, and again at a temperature rise rate of 1° C./sec from the fourth wave end point L. After that, no gas extraction was observed until the analysis was completed. The oxygen content corresponding to the first wave was 0.9 ppm, the oxygen content corresponding to the second wave was 1.1 ppm, the oxygen content corresponding to the third wave was 0.7 ppm, the oxygen content corresponding to the fourth wave was 1.2 ppm, and the total oxygen content was 3.9 ppm. Oxides reacted at these respective temperatures were determined by equilibrium calculation. As a result, it was found that the first wave represents $SiO_2$, the second wave represents $Al_2O_3$, the third wave represents MgO, and the fourth wave represents CaO. This was in agreement with the results obtained from investigation of the proportions of ingredients constituting the oxides by means of X-ray microanalyzer.

Figure 10:
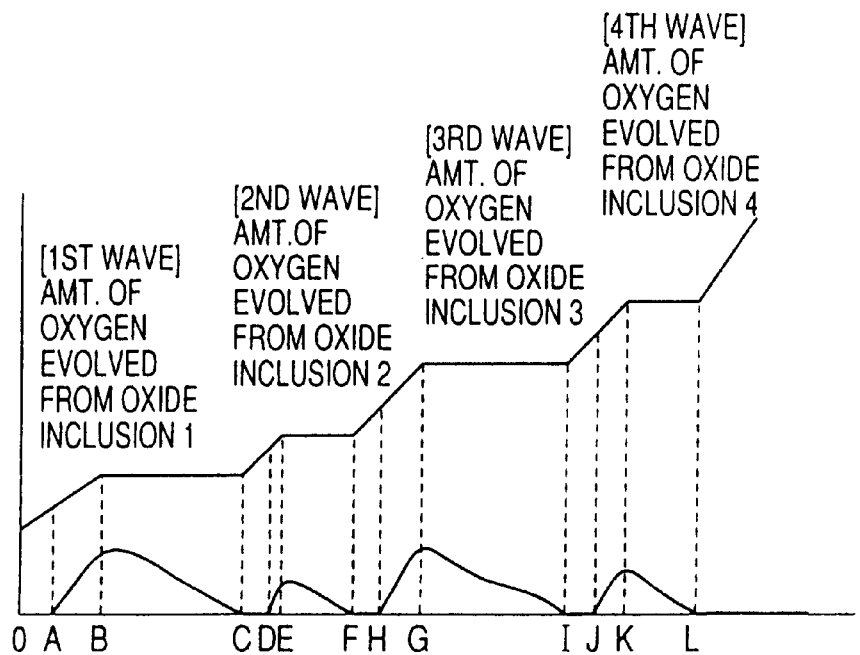
FIG. 10 is an explanatory view showing an extraction curve for oxygen according to Comparative Example 13.

In Comparative Example 13, analysis was carried out in the same manner as described above in connection with the method according to the present invention, except that the temperature rise rate was 3° C./sec, that is, was higher than that in the method according to the present invention. Despite the use of the same bearing steel as used in Example 10, as shown in FIG. 10, the wave separability was poor, and two waves could not be separated form each other. As a result, oxygen contents for respective oxide inclusions could not be determined.

In Examples 8 to 10, waves for respective CO gases derived from oxide inclusions could be clearly separated from each other or one another, and the analyte could be analyzed for oxygen in each oxide inclusion.

In all the above examples, the evolved oxygen is one from oxide inclusions extracted from a temperature of 900° C. or above, and the true oxygen content of the metal analyte could be determined for each oxide inclusion.

As described above, application of the analytical method according to the method of the present invention to the analysis for oxygen by the inert gas fusion carrying/infrared absorption method realized separation and determination of oxygen for each oxide inclusion in the metal analyte with good accuracy.

TABLE 4

| | Items | Comp. Ex. 10 | Comp. Ex. 11 | Comp. Ex. 12 | Comp. Ex. 13 |
|---|---|---|---|---|---|
| Temp. rise rate, °C./sec | Temp. rise rate in period from analyte heating start point 0 to 1st wave start point A | 1 | 1 | 1 | 3 |
| | Temp. rise rate in period from 1st wave start point A to 1st wave peak appearance point B | 1 | 1 | 1 | 3 |
| | Temp. rise rate in period from 1st wave peak appearance point B to 1st wave end point C | 1 | 1 | 1 | 0 |
| | Temp. rise rate in period from 1st wave end point C to 2nd wave peak appearance point E | 1 (wave appearance ended, temp. raised until completion of analysis) | 1 (Wave appearance ended, temp. raised until completion of analysis) | 3 (Wave appearance ended, temp. raised until completion of analysis) | 3 |
| | Temp. rise rate in period from 2nd wave peak appearance point E to 2nd wave end point F | | | | 0 |
| | Temp. rise rate in period from 2nd wave end point F to 3rd wave peak appearance point H | — | — | — | 3 (Wave appearance ended, temp. raised until completion of analysis) |
| | Temp. rise rate in period from 3rd wave peak appearance point H to 3rd wave end point L | — | — | — | |
| | Temp. rise rate in period from 3rd wave end point L to 4th wave peak appearance point K | — | — | — | — |
| | Temp. rise rate in period from 4th wave peak appearance point K to 4th wave end point L | — | — | — | — |
| | Temp. rise rate in period from 4th wave end point L to completion of analysis | — | — | — | — |
| Number of waves | | 1 | 1 | 1 | 1 |
| Total oxygen content, ppm | 1st wave | 12.1 | 3.8 | 3.9 | 2.0 |
| | 2nd wave | — | — | — | 1.9 |
| Peak appearance temp., °C. | | | | | |
| | 3rd wave | — | — | — | — |
| | 4th wave | — | — | — | — |
| Type of metal analyte | | Carbon steel for mechanical structure | Bearing steel | Bearing steel | Bearing steel |

| | Items | Ex. 8 | Ex. 9 | Ex. 10 |
|---|---|---|---|---|
| Temp. rise rate, °C./sec | Temp. rise rate in period from analyte heating start point 0 to 1st wave start point A | 1 | 1 | 1 |
| | Temp. rise rate in period from 1st wave start point A to 1st wave peak appearance point B | 1 | 1 | 1 |
| | Temp. rise rate in period from 1st wave peak appearance point B to 1st wave end point C | 0 | 0 | 0 |
| | Temp. rise rate in period from 1st wave end point C to 2nd wave peak appearance point E | 1 | 1 | 1 |
| | Temp. rise rate in period from 2nd wave peak appearance point E to 2nd wave end point F | 0 | 0 | 0 |
| | Temp. rise rate in period from 2nd wave end point F to 3rd wave peak appearance | 1 (Wave appearance ended, temp. | 1 | 1 |

TABLE 4-continued

|  |  |  | | |
|---|---|---|---|---|
| | point H Temp. rise rate in period from 3rd wave peak appearance point H to 3rd wave end point L | raised until completion of analysis) | 0 | 0 |
| | Temp. rise rate in period from 3rd wave end point L to 4th wave peak appearance point K | — | 1 (Wave appearance ended, temp. raised until completion of analysis) | 1 |
| | Temp. rise rate in period from 4th wave peak appearance point K to 4th wave end point L | — | — | 0 |
| | Temp. rise rate in period from 4th wave end point L to completion of analysis | — | — | 1 (Wave appearance ended, temp. raised until completion of analysis) |
| Number of waves | | 2 | 3 | 4 |
| Total oxygen content, ppm | 1st wave | 3.8($SiO_2$) 1350 | 1.1($SiO_2$) 1350 | 0.9($SiO_2$) 1350 |
| Peak appearance temp., °C. | 2nd wave | 10.3($Al_2O_3$) 1470 | 1.4($Al_2O_3$) 1470 | 1.1($Al_2O_3$) 1470 |
| | 3rd wave | — — | 1.3(CaO) 1620 | 0.7(MgO) 1620 |
| | 4th wave | — — | — — | 1.2(CaO) 1720 |
| Type of metal analyte | | Carbon steel for mechanical structure | Bearing steel | Bearing steel |

EXAMPLES 11 to 14

Examples 11 to 14 of the present invention, together with Comparative Examples 14 and 15, will be described with reference to FIG. 13 and Table 5.

Figure 13:
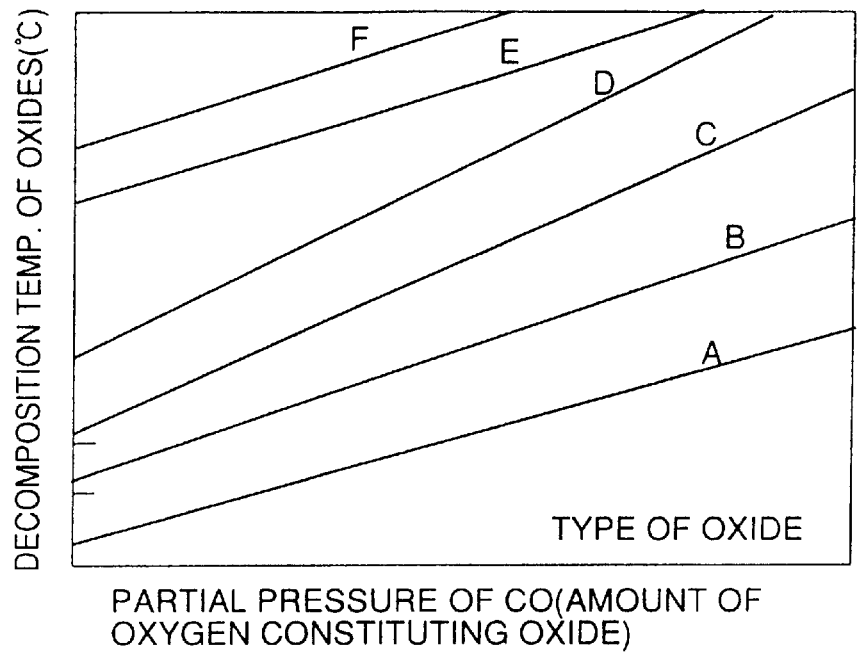
FIG. 13 is a schematic diagram showing the construction of a sample analyzer according to an embodiment of the present invention.

FIG. 13 is a schematic diagram showing the construction of a principal part of a sample analyzer applied to the method according tot he present invention. In FIG. 13, numeral 1 designates an extractor of direct energization system. In the interior of the extractor, a crucible 2, in which an analyte is to be placed, is sandwiched between an upper electrode 3 and a lower electrode 34 for energization heating of the crucible. Numeral 5 designates an alternating current source, and one end thereof is connected to the upper electrode 3 through an ammeter 6, and the other end is connected to the lower electrode 4. Numeral 7 designates a voltmeter for measuring the voltage across both the electrodes 3, 4.

Numeral 16 designates a gas passage for the sample analyzer. A flow rate controller 8 for regulating the flow rate of a gas introduced into the extractor 1 and a flow rate controller 9 for regulating the flow rate of a gas introduced into an infrared CO absorption detector 10 are connected to the gas passage 16, and the analyte is analyzed in the infrared CO absorption detector 10 to determine the oxygen content. After the infrared CO absorption detector 10, in order to analyze the analyte for nitrogen, a thermal conductive analyzer 14 is connected to a room temperature oxidizer 11 for selectively oxidizing CO contained in the gas to convert CO to $CO_2$, a $CO_2$ remover 12 for selectively removing $CO_2$ alone produced in the room temperature oxidizer, and an $H_2O$ remover 13.

Numeral 17 designates an electric signal control circuit that sends an extracted gas signal to a microcomputer 15 and, at the same time, send a signal, for regulating the amount of helium in the atmosphere gas, to the gas flow rate control valves 8, 9.

Numeral 15 designates a computation control section, such as a microcomputer, which computes the extracted gas signal from the sample to quantitatively determine the oxygen content and the nitrogen content for each oxide inclusion.

For the following examples and comparative examples, the analysis was carried out using the analyzer shown in FIG. 13. Conditions and results for each example are summarized in Table 5.

TABLE 5

| Items | | Comp. Ex. 14 | Comp. Ex. 15 | Ex. 11 | Ex. 12 | Ex. 13 |
|---|---|---|---|---|---|---|
| Amount of analyte melted, g | | 0.5 | 1 | 0.5 | 1 | 3 |
| Type of analyte | | Powder | Metal (bearing steel) | Powder | Metal (bearing steel) | Metal (Bearing steel) |
| Composition for each form and oxygen equivalent amount of analyte, mg or ppm | $Al_2O_3$ | 0.141 mg | 2.5 ppm | 0.141 mg | 2.5 ppm | 2.5 ppm |
| | MgO | 0.040 mg | 1.5 ppm | 0.040 mg | 1.5 ppm | 1.5 ppm |
| | CaO | 0.028 mg | 1.0 ppm | 0.028 mg | 1.0 ppm | 1.0 ppm |

TABLE 5-continued

| Items | | | Comp. Ex. 14 | Comp. Ex. 15 | Ex. 11 | Ex. 12 | Ex. 13 |
|---|---|---|---|---|---|---|---|
| Temp. rise rate of analyte, ° C./sec | | | 10 | 10 | 10 | 10 | 10 |
| Flow Rate of Inert gas, ml/min. | Flow rate controller 8 | Until 1st wave peak appearance | 400 | 400 | 600 | 600 | 600 |
| | | From 1st wave peak appearance to 2nd wave peak appearance | 400 | 400 | 500 | 500 | 500 |
| | | From 2nd wave peak appearance to 3rd wave peak appearance | 400 | 400 | 400 | 400 | 400 |
| | | From 3rd wave peak appearance to completion of analysis | 400 | 400 | 300 | 300 | 300 |
| | Flow rate controller 9 | Until 1st wave peak appearance | 400 | 400 | 600 | 600 | 600 |
| | | From 1st wave peak appearance to 2nd wave peak appearance | 400 | 400 | 500 | 500 | 500 |
| | | From 2nd wave peak appearance to 3rd wave peak appearance | 400 | 400 | 400 | 400 | 400 |
| | | From 3rd wave peak appearance to completion of analysis | 400 | 400 | 300 | 300 | 300 |
| Optical path length of infrared CO absorption detector, mm | | | 50 | 50 | 50 | 50 | 50 |
| Separability of waves, number of waves | | | 1 | 1 | 3 | 3 | 3 |
| Results of extraction of oxygen for each form, mg or ppm | | $Al_2O_3$ | 0.201 mg in total | 4.9 ppm in total | 0.141 mg | 2.49 ppm | 2.50 ppm |
| | | MgO | | | 0.040 mg | 1.48 ppm | 1.49 ppm |
| | | CaO | | | 0.028 mg | 0.96 ppm | 0.98 ppm |

In Comparative Example 14, an artificially prepared oxide powder was analyzed. The amount of the powder melted was 0.5 g. An $Al_2O_3$ powder, an MgO powder, and a CaO powder were accurately weighed with a balance so that, in the powder, the amount of oxygen as $Al_2O_3$ is 0.141 mg, the amount of oxygen as MgO is 0.040 mg, and the amount of oxygen as CaO is 0.028 mg. These three powders were mixed together, and the mixture was placed in a graphite crucible 2 which has been previously deaerated under conditions of 2773 K and atmosphere gas helium flow rate 2000 ml/min. At the time of gas extraction, the flow rate of atmosphere gas helium, which flows through the gas flow rate controllers 8, 9, was brought to 400 ml/min. The extracted gas was introduced into the infrared CO absorption detector (optical path length 50 mm) through the gas passage 16 and analyzed by the infrared CO absorption mechanism, and the amount of the oxygen gas was computed by the microcomputer 15. The temperature rise rate of the analyte was 10° C./sec. As a result, a first wave only appeared without separation into a plurality of waves, that is, three waves as shown in FIG. 11. The total amount of oxygen was 0.201 mg, indicating that the introduced oxygen could be substantially recovered.

In Example 11, regarding the analyte, the powders and the mixing ratio of these powders were the same as in Comparative Example 14. Further, the analytical conditions except for the inert gas flow rate were also the same as those in Comparative Example 14. The inert gas flow rate was regulated as follows. Until the appearance of a peak of the first wave, the flow rate of the atmosphere gas, which flows through the gas flow rate controllers 8, 9, was brought to 600 ml/min. Thereafter, after the completion of appearance of the peak of the first wave, the flow rate of the atmosphere gas, which flows through the gas flow rate controllers 8, 9, was reduced to 500 ml/min. This permitted a second wave to appear separately from the first wave.

Until the appearance of the second wave peak, the flow rate of the atmosphere gas, which flows through the gas flow rate controllers 8, 9, was kept at 500 ml/min. After the appearance of the second wave peak, the temperature was further raised, and the flow rate of the atmosphere gas, which flows through the gas flow rate controllers 8, 9 was reduced to 400 ml/min. This permitted a third wave to appear separately from the second wave. Until the appearance of the third wave peak, the flow rate of the atmosphere gas, which flows through the gas flow rate controllers 8, 9, was kept at 400 ml/min. After the appearance of the third wave peak, the temperature was further raised, and the flow rate of the atmosphere gas, which flows through the gas flow rate controllers 8, 9 was reduced to 300 ml/min. No further wave appears, and the gas extraction was completed.

The first wave is one showing the amount of oxygen corresponding to $Al_2O_3$ oxide, and the amount of oxygen was 0.141 mg. The second wave is one showing the amount of oxygen corresponding to MgO oxide, and the amount of oxygen was 0.040 mg. The third wave is one showing the amount of oxygen corresponding to CaO oxide, and the amount of oxygen was 0.028 mg. It is considered that, in the analysis, a reduction in flow rate of inert gas in the order of appearance of waves increases the partial pressure of CO at the time of gas extraction and the decomposition temperature of oxides are shifted toward higher temperature side, resulting in improved wave separation. Thus, regulation of the inert gas flow rate in the course of the analysis has enabled analysis for oxygen in each of three oxides in the powder analyte.

In Comparative Example 15, a bearing steel was analyzed. Inclusions of the bearing steel were $Al_2O_3$, MgO, and CaO. The oxygen content of the analyte for each inclusion was quantitatively determined by extraction separation of inclusions. As a result, it was found that the content of oxygen corresponding $Al_2O_3$ was 2.5 ppm, the content of oxygen corresponding to MgO was 1.5 ppm, and the content of oxygen corresponding to CaO was 1.0 ppm. Conditions for analysis, such as temperature rise rate, inert gas flow rate, and optical path length of infrared CO absorption detector were the same as those in Comparative Example 14. The extracted wave could not be separated into three and was single, and the total exacted oxygen content was 4.9 ppm.

In Example 12, regarding the analyte, the same bearing steel as used in Comparative Example 15 was analyzed. Further, the analytical conditions except for the inert gas flow rate were also the same as those in Comparative Example 15. The inert gas flow rate was regulated as follows. Until the appearance of a peak of the first wave, the flow rate of the atmosphere gas, which flows through the gas flow rate controllers 8, 9, was brought to 600 ml/min. Thereafter, after the completion of appearance of the peak of the first wave, the flow rate of the atmosphere gas, which flows through the gas flow rate controllers 8, 9, was reduced to 500 ml/min. This permitted a second wave to appear clearly separately from the first wave. Until the appearance of a second wave peak, the flow rate of the atmosphere gas, which flows through the gas flow rate controllers 8, 9, was kept at 500 ml/min. After the appearance of the second wave peak, the temperature was further raised, and the flow rate of the atmosphere gas, which flows through the gas flow rate controllers 8, 9 was reduced to 400 ml/min. This permitted a third wave to appear clearly separately from the second wave. Until the appearance of a third wave peak, the flow rate of the atmosphere gas, which flows through the gas flow rate controllers 8, 9, was kept at 400 ml/min. After the appearance of the third wave peak, the temperature was further raised, and the flow rate of the atmosphere gas, which flows through the gas flow rate controllers 8, 9, was reduced to 300 ml/min. No further wave appeared, and the gas extraction was completed. The first wave is an extraction curve for oxygen corresponding to $Al_2O_3$ inclusion, and the oxygen content was 2.49 ppm. The second wave is an extraction curve for oxygen corresponding to MgO inclusion, and the oxygen content was 1.48 ppm. The third wave is an extraction curve for oxygen corresponding to CaO inclusion, and the oxygen content was 0.96 ppm.

It is considered that, as with the analysis of the powder analyte, in the analysis, a reduction in flow rate of inert gas in the order of appearance of waves increases the partial pressure of CO in the crucible 2 at the time of gas extraction and the decomposition temperature of oxides are shifted toward higher temperature side as compared with the case where the atmosphere gas flow rate is kept constant, resulting in improved wave separation. Thus, regulation of the inert gas flow rate in the course of the analysis has enabled analysis for oxygen in each of three oxides in the bearing steel as the analyte.

In Example 13, the same bearing steel as used in Comparative Example 15 and Example 12 was analyzed. In Example 13, the amount of the analyte melted was increased to 3 g as compared with 1 g of the analyte melted in Comparative Example 15 and Example 12. Other conditions, such as melting and gas flow rate, were quite the same as those used in Example 12. As compared with Example 12, the absolute amount of oxygen evolved from each oxide was increased, the separability of the first, second, and third waves from one another was further improved, resulting in improved accuracy of the quantitatively determined value for each oxide.

In Example 14 (not shown in Table 5), 1 g of a bearing steel was analyzed while simultaneously controlling the temperature rise rate and the gas flow rate. Inclusions of the bearing steel were $SiO_2$, $Al_2O_3$, MgO, and CaO. The oxygen content of the analyte for each inclusion was previously quantitatively determined by extraction separation of inclusions. As a result, it was found that the content of oxygen corresponding to $SiO_2$ was 0.8 ppm, the content of oxygen corresponding to $Al_2O_3$ was 2.1 ppm, the content of oxygen corresponding to MgO was 1.4 ppm, and the content of oxygen corresponding to CaO was 1.0 ppm. The analyte was heated at a temperature rise rate of 1° C./sec in a period from a analyte heating start point to a first wave peak appearance point and at a temperature rise rate of 0° C./sec in a period from the first wave peak appearance point to a first wave end point. In this case, until the appearance of a peak of the first wave, the flow rate of the atmosphere gas, which flows through the gas flow rate controllers 8, 9, was 600 ml/min. Thereafter, in a period from the completion of appearance of the peak of the first wave to a second wave peak appearance point, the flow rate of the atmosphere gas, which flows through the gas flow rate controllers 8, 9, was reduced to 500 ml/min. This permitted a second wave to appear clearly separately from the first wave. The temperature rise rate in a period from the first wave end point to the second wave peak appearance point was 1° C./sec.

The temperature rise rate in a period from the second wave peak appearance point to a second wave end point was again brought to 0° C./sec. As soon as the second wave peak appears, the flow rate of the atmosphere gas, which flows through the gas flow rate controllers 8, 9, was reduced to 400 ml/min until a third wave peak appeared. This permitted the third wave to appear clearly separately from the second wave. The temperature rise rate in a period from the second wave end point to the third wave peak appearance point was 1° C./sec.

The temperature rise rate in a period from the third wave peak appearance point to a third wave end point was again brought to 0° C./sec. As soon as the third wave peak appeared, the flow rate of the atmosphere gas, which flows through the gas flow rate controllers 8, 9, was reduced to 350 ml/min until a fourth wave peak appeared. This permitted the fourth wave to appear clearly separately from the third wave. The temperature rise rate in a period from the third wave end point to the fourth wave peak appearance point was 1° C./sec.

The temperature rise rate in a period from the fourth wave peak appearance point to a fourth wave end point was again brought to 0° C./sec. As soon as the fourth wave peak appeared, the flow rate of the atmosphere gas, which flows through the gas flow rate controllers 8, 9, was reduced to 300 ml/min. The temperature rise rate was again brought to 1° C./sec from the fourth wave end point. As a result, no further gas extraction occurred until the completion of the analysis. The first wave is an extraction curve for oxygen corresponding to $SiO_2$ and indicates that the oxygen content is 0.79 ppm. The second wave is an extraction curve for oxygen corresponding to $Al_2O_3$ and indicates that the oxygen content is 2.1 ppm. The third wave is an extraction curve for oxygen corresponding to MgO and indicates that the oxygen content is 1.4 ppm. The fourth wave is an extraction curve for oxygen corresponding to CaO and indicates that the oxygen content is 1.0 ppm. Thus, analysis while simultaneously controlling the temperature rise rate and the gas flow rate could provide results which were in very good agreement with the oxygen contents of the analyte for each inclusion which had been previously quantitatively determined. Further, the peak position of each wave could be more clearly distinguished as compared with that in the case where only the gas flow rate was controlled.

The effect of separating waves from each other or one another according to the examples of the present invention better with reducing the temperature rise rate of the analyte at the time of gas extraction.

The flow rate of the gas passing through the flow rate controller 8 may be the same as that of the gas passing through the flow rate controller 9. However, peakout of the display of exacted wave often occurs due to excessive amount of extracted gas. In this case, the flow rate of the gas passing through the flow rate controller 9 may be reduced.

As is apparent from the foregoing description, application of the apparatus according to the present invention to the analysis for oxygen for each oxide by the inert gas fusion carrying/infrared absorption method realized separation and determination of oxygen for each oxide inclusion in an analyte with good accuracy.

What is claimed is:

1. A method for analyzing a metal for oxygen, using inert gas carrying fusion/infrared absorption analysis, comprising the steps of:

placing a metal analyte in a graphite crucible;

heat-melting the metal analyte;

extracting a gas from the melt bath; and analyzing the gas to determine the total oxygen content of the metal in the form of a plurality of separated waves, wherein the metal analyte is heated at a temperature rise rate of not more than 20° C./sec in a period from a starting point A of a first wave to a peak point B of the first wave, held at a constant temperature in a period from the peak point B of the first wave to an end point C of the first wave, and, after the completion of the appearance of the first wave, is further heated to melt the metal analyte for further analysis.

2. The method for analyzing a metal for oxygen according to claim 1 wherein, in the inert gas carrying fusion/infrared absorption analysis comprising the steps of:

placing a metal analyte in a graphite crucible;

heat-melting the metal analyte;

extracting a gas from the melt bath; and analyzing the gas to determine the total oxygen content of the metal in the form of a plurality of separated waves, wherein the metal analyte is analyzed without pretreatment for removing an oxide film as a contaminant formed on the surface of the metal analyte.

3. A method for analyzing a metal for oxygen in each oxide inclusion, comprising the steps of:

placing a metal analyte in a graphite crucible in an inert gas atmosphere;

heat-melting the metal analyte;

extracting a CO gas from the melt bath; and analyzing the gas to determine the oxygen content of the metal in the form of a plurality of waves, wherein, for each wave which appears at a temperature of 900° C. or above, the following temperature control pattern of ①, ②, and ③ is repeated:

① the analyte is heated at a temperature rise rate of not more than 2° C./sec in a period from a starting point $A_n$ of each wave to a peak point $B_n$ of each wave;

② the analyte is held at a constant temperature in a period from the peak point $B_n$ of each wave to an end point $C_n$ of each wave; and ③ the analyte is heated at a temperature rise rate of not more than 2° C./sec in a period from the end point $C_n$ of each wave to a starting point $A_{n-1}$ of the next wave.

* * * * *